(12) United States Patent
Kanai et al.

(10) Patent No.: US 9,932,333 B2
(45) Date of Patent: Apr. 3, 2018

(54) BENZOTHIAZOLE COMPOUND AND MEDICINE CONTAINING SAME

(71) Applicant: JAPAN SCIENCE AND TECHNOLOGY AGENCY, Kawaguchi-shi (JP)

(72) Inventors: Motomu Kanai, Bunkyo-ku (JP); Yohei Soma, Bunkyo-ku (JP); Atsuhiko Taniguchi, Hachioji (JP); Yusuke Shimizu, Chuo-ku (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 15/326,320

(22) PCT Filed: Jul. 15, 2015

(86) PCT No.: PCT/JP2015/070317
§ 371 (c)(1),
(2) Date: Jan. 13, 2017

(87) PCT Pub. No.: WO2016/010092
PCT Pub. Date: Jan. 21, 2016

(65) Prior Publication Data
US 2017/0197956 A1 Jul. 13, 2017

(30) Foreign Application Priority Data
Jul. 16, 2014 (JP) .................................. 2014-145736

(51) Int. Cl.
*C07D 455/04* (2006.01)
*C07D 417/04* (2006.01)

(52) U.S. Cl.
CPC ......... *C07D 455/04* (2013.01); *C07D 417/04* (2013.01)

(58) Field of Classification Search
CPC ........................... C07D 455/04; C07D 417/04
See application file for complete search history.

(56) References Cited

U.S. PATENT DOCUMENTS

| 5,091,298 A * | 2/1992 | Parton ................. C09B 23/0075 430/570 |
| 2006/0100196 A1 | 5/2006 | Gailunas et al. |
| 2007/0185144 A1 | 8/2007 | Zhong et al. |
| 2009/0036478 A1 | 2/2009 | Zhong et al. |
| 2010/0222338 A1 | 9/2010 | Zhong et al. |
| 2013/0072483 A1 | 3/2013 | Zhong et al. |

FOREIGN PATENT DOCUMENTS

| JP | 2002-202598 A | 7/2002 |
| JP | 2005-514330 A | 5/2005 |
| JP | 2009-516684 A | 4/2009 |
| JP | 2010-85465 A | 4/2010 |
| JP | 2010-528015 A | 8/2010 |
| WO | WO 2007/086800 A1 | 8/2007 |

OTHER PUBLICATIONS

A. Srivastava, et al., "Identifying the Bond Responsible for the Fluorescence Modulation in an Amyloid Fibril Sensor," Chemistry—A European Journal, 2010, vol. 16, No. 30, pp. 9257-9263.
D. L. Garmaise, et al., "Anthelmintic Quaternary Salts. III. Benzothiazolium Salts," Journal of Medicinal Chemistry, 1969, vol. 12, No. 1, pp. 30-36.
L. Hou, et al., "Methionine 35 Oxidation Reduces Fibril Assembly of the Amyloid Aβ-(1-42) Peptide of Alzheimer's Disease," The Journal of Biological Chemistry, Oct. 25, 2002, vol. 277, No. 43, pp. 40173-40176.
G. Bitan, et al., "A Molecular Switch in Amyloid Assembly: Met$^{35}$ and Amyloid β-Protein Oligomerization," Journal of the American Chemical Society, 2003, vol. 125, No. 50, pp. 15359-15365.
J. Moskovitz, et al., "Induction of Methionine-Sulfoxide Reductases Protects Neurons from Amyloid β-Protein Insults in Vitro and in Vivo," Biochemistry, 2011, No. 50, pp. 10687-10697.
A. Taniguchi, et al., "Attenuation of the Aggregation and Neurotoxicity of Amyloid-β Peptides by Catalytic Photooxygenation," Angewandte Chem. International Edition, 2014, vol. 53, pp. 1382-1385.

(Continued)

*Primary Examiner* — D Margaret M Seaman
(74) *Attorney, Agent, or Firm* — Oblon, McClelland, Maier & Neustadt, L.L.P.

(57) ABSTRACT

It is intended to provide: a compound useful as an amyloid oxidation catalyst which is applicable in vivo and is applicable not only to Aβ peptides but to other amyloids; and a prophylactic or therapeutic drug for an amyloid-related disease, comprising the same. The present invention provides a benzothiazole compound represented by the following formula (1) wherein X represents a halogen atom; $R^1$ represents an optionally substituted hydrocarbon group; $R^2$ represents a hydrogen atom or an optionally substituted hydrocarbon group; $R^3$ and $R^4$ are the same or different and each represent a hydrogen atom, an optionally substituted hydrocarbon group, an alkoxy group, a halogen atom, an amino group, a nitro group, or a cyano group; $R^2$ and $R^4$ optionally together form an alkylene group; and $R^5$ represents an anion.

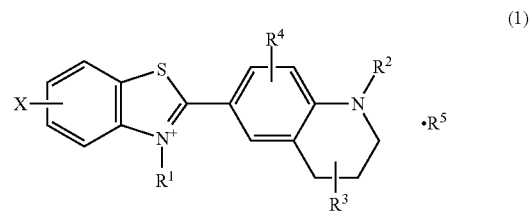

(1)

12 Claims, 29 Drawing Sheets

(56) References Cited

OTHER PUBLICATIONS

International Search Report dated Oct. 13, 2015 in PCT/JP2015/070317.
Extended European Search Report dated Nov. 7, 2017 in Patent Application No. 15822530.0.
Sabrina Noel, et al., "The benzazole scaffold: a SWAT to combat Alzheimer's disease", Chemical Society Reviews, vol. 42, No. 19, 2013, XP055418223A, p. 7747-7762.

* cited by examiner

[Figure 1]
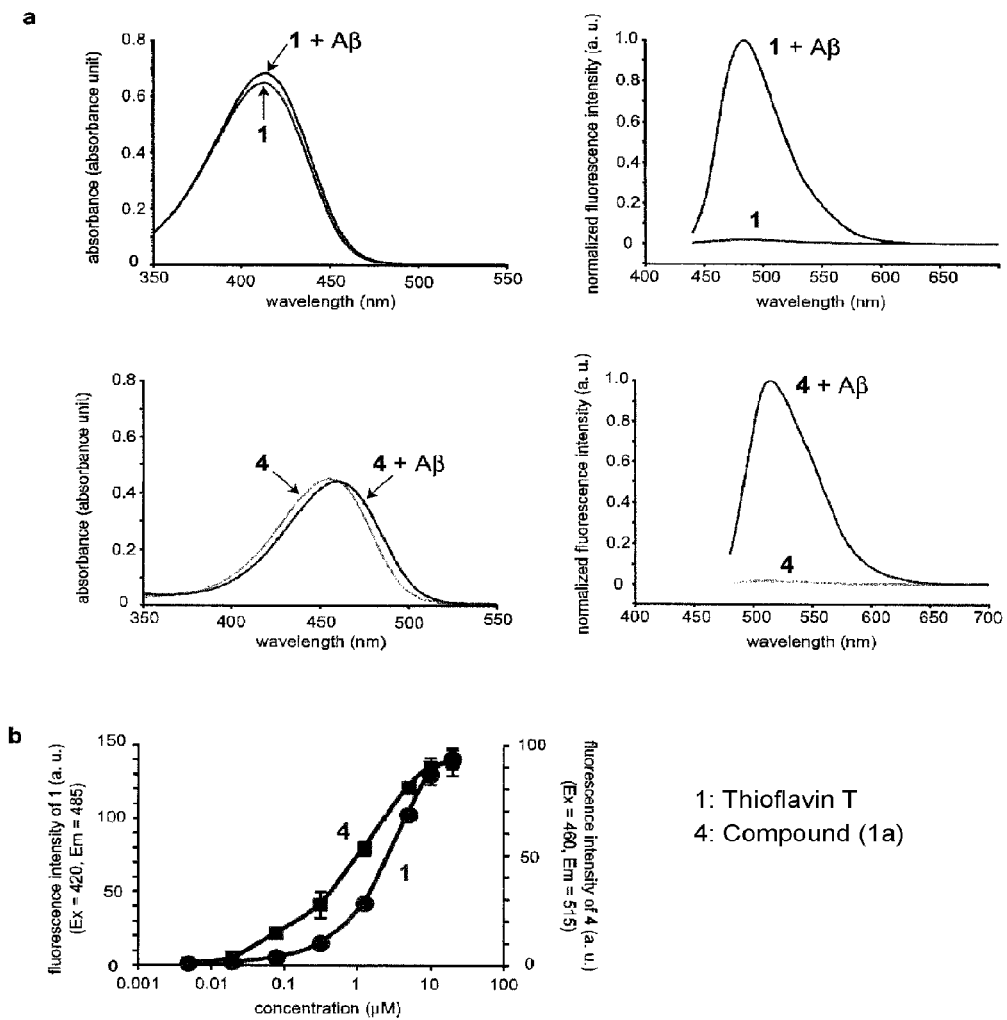
1: Thioflavin T
4: Compound (1a)

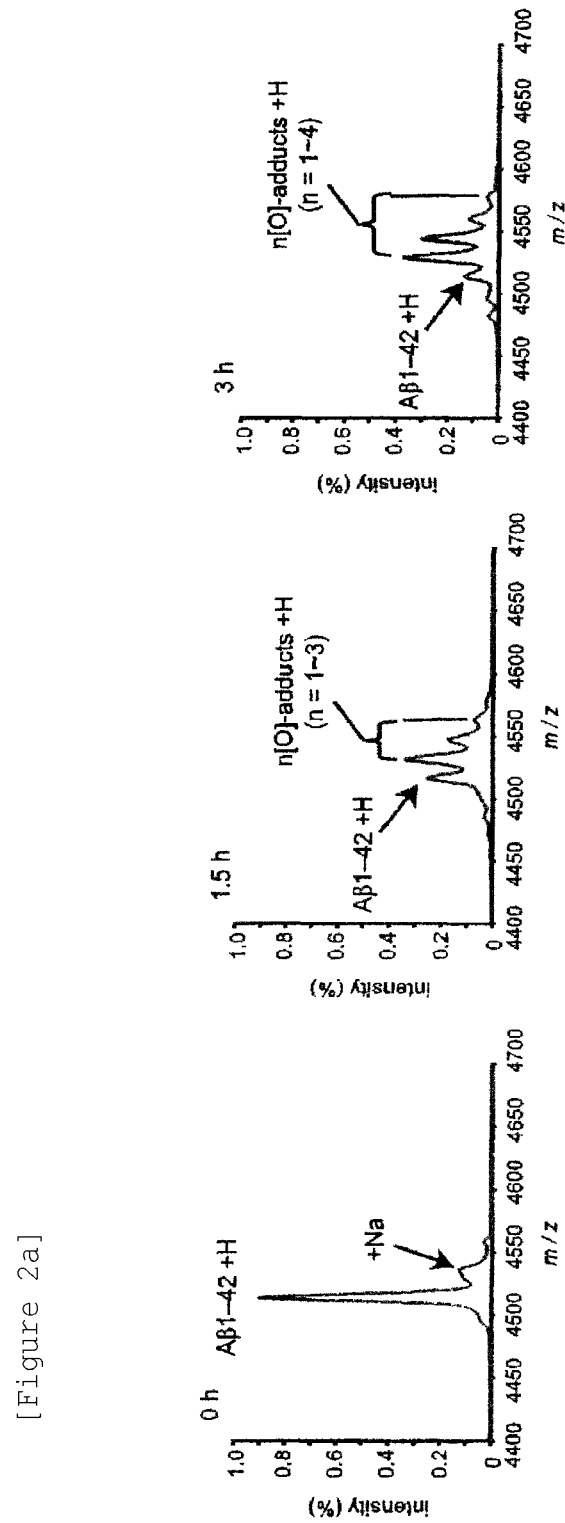
[Figure 2a]

[Figure 2b]
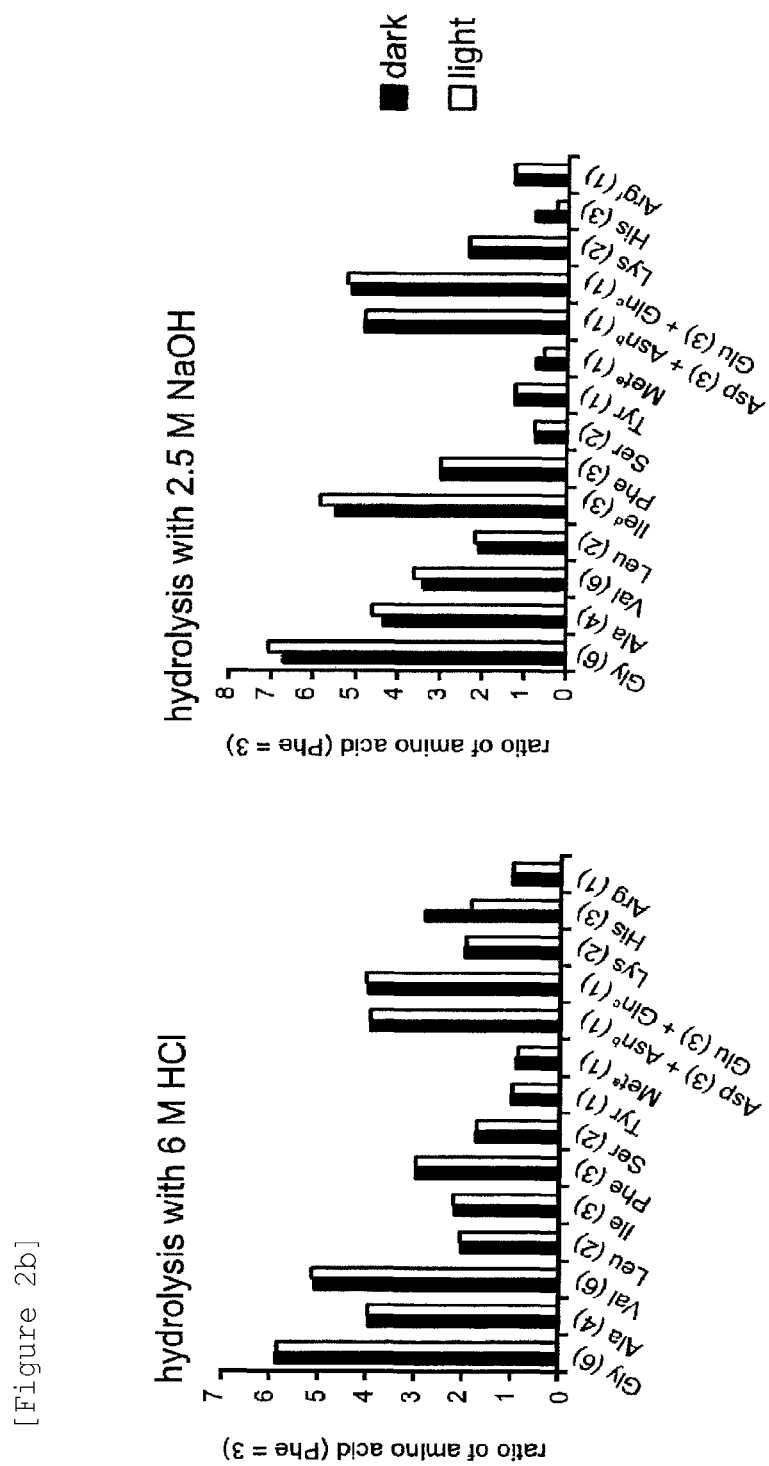

[Figure 2c]
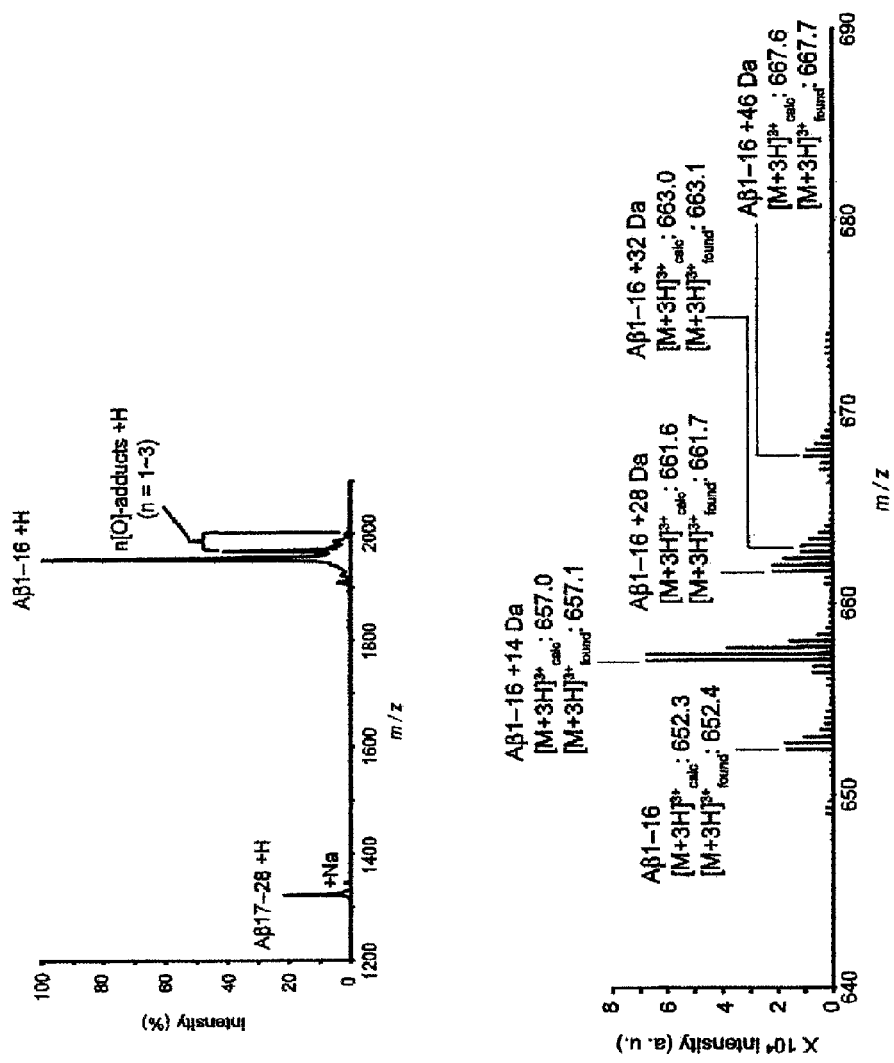

[Figure 2d]
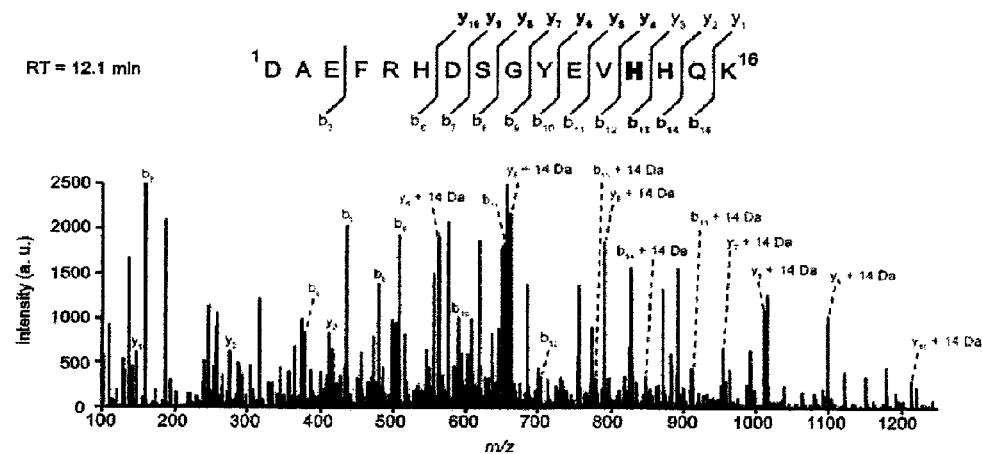
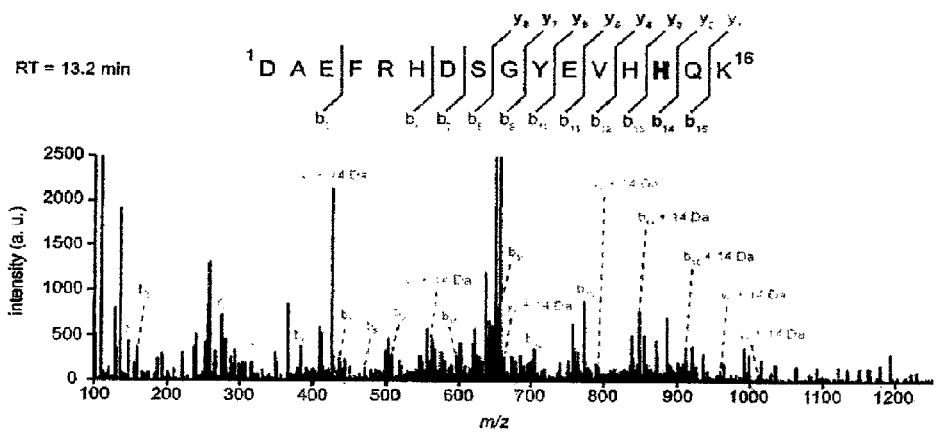

[Figure 3a]
amyloid-β peptide 1-42 (Aβ1-42): $\overset{1}{\text{D}}$AEFR HDSG$\overset{10}{\text{Y}}$ EVHHQ KLVF$\overset{20}{\text{F}}$ AEDVG SNKG$\overset{30}{\text{A}}$ IIGL$\underline{\text{M}}$ VGG$\overset{40}{\text{V}}$V I$\overset{42}{\text{A}}$
[Figure 3b]
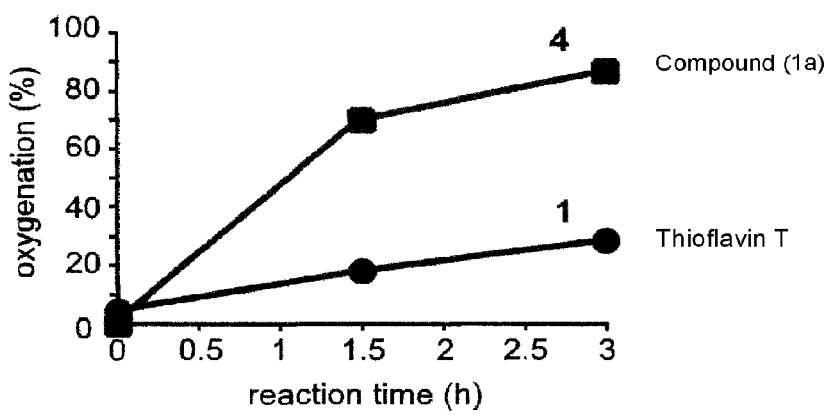
[Figure 3c]
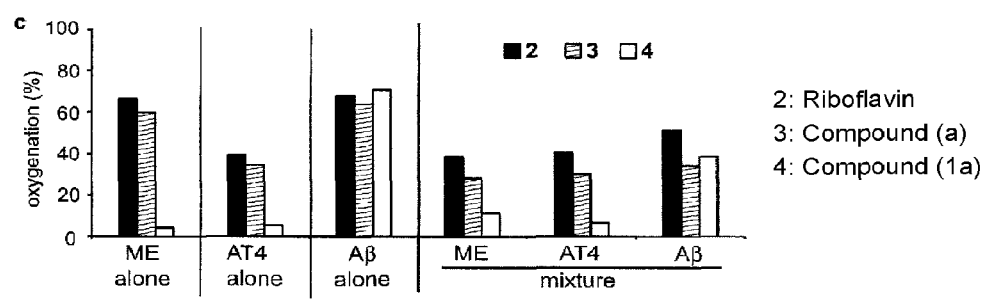
2: Riboflavin
3: Compound (a)
4: Compound (1a)

[Figure 3d]
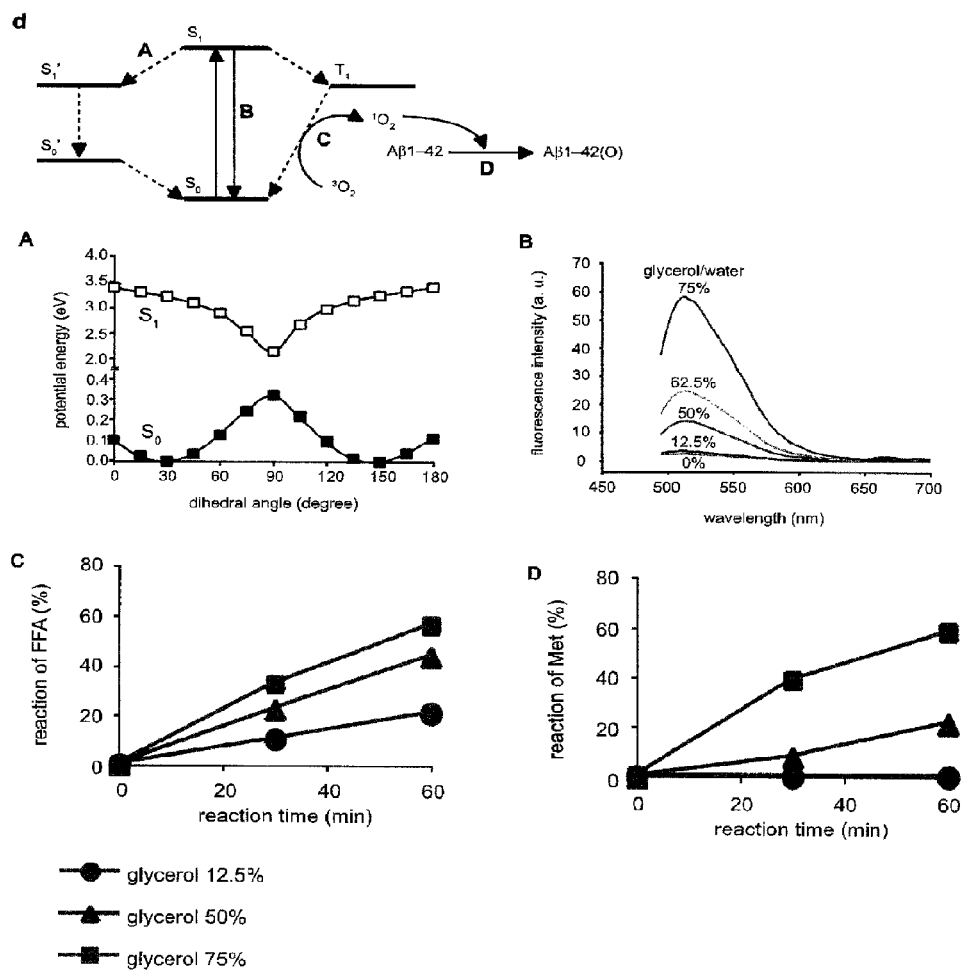

[Figure 4]
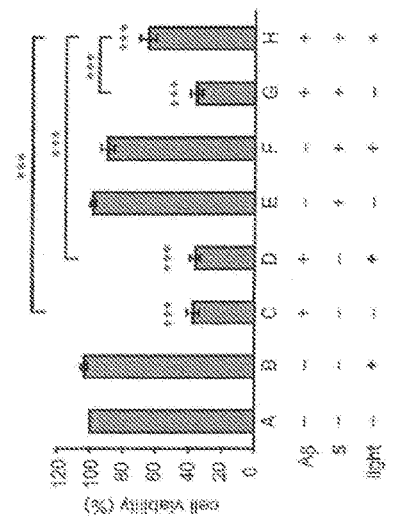
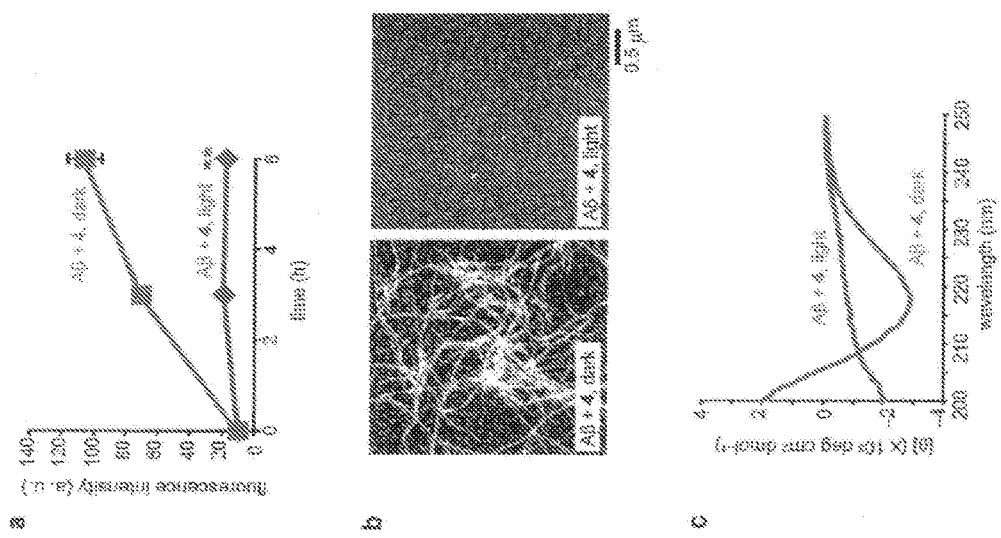
4: Compound (1a)
5: Compound (1e)

[Figure 5]
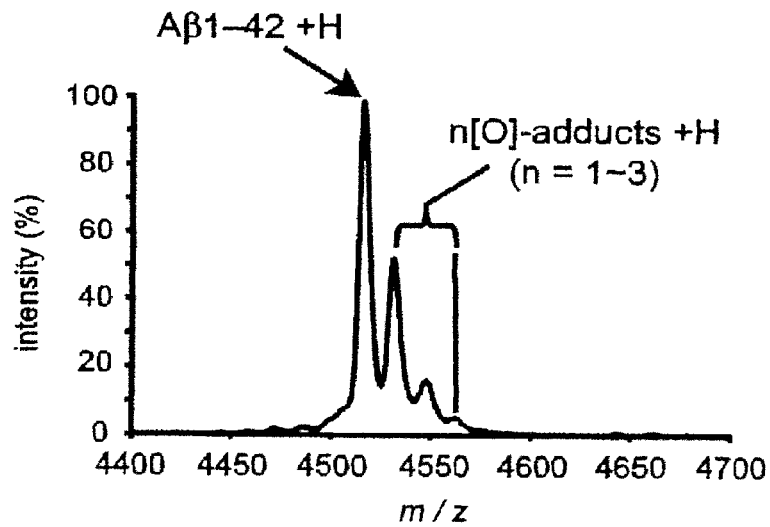
[Figure 6a]
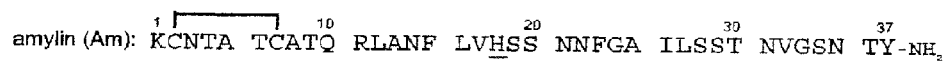
[Figure 6b]
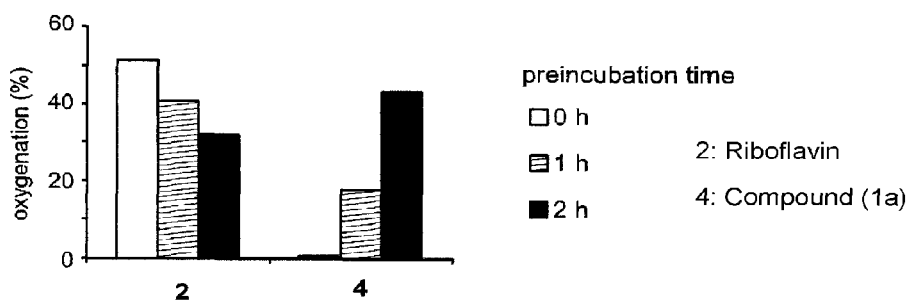
preincubation time
□ 0 h
▤ 1 h      2: Riboflavin
■ 2 h      4: Compound (1a)

[Figure 6c]
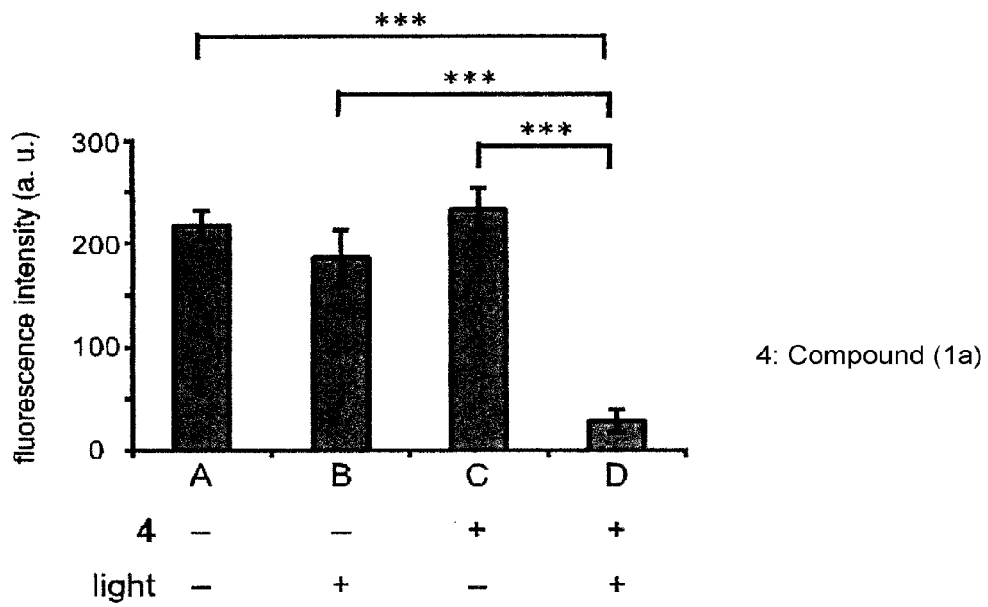
4: Compound (1a)
[Figure 6d]
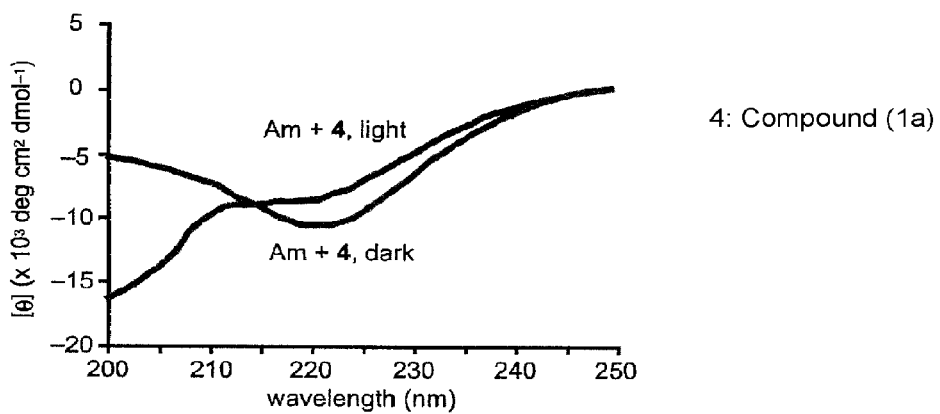
4: Compound (1a)

[Figure 6e]
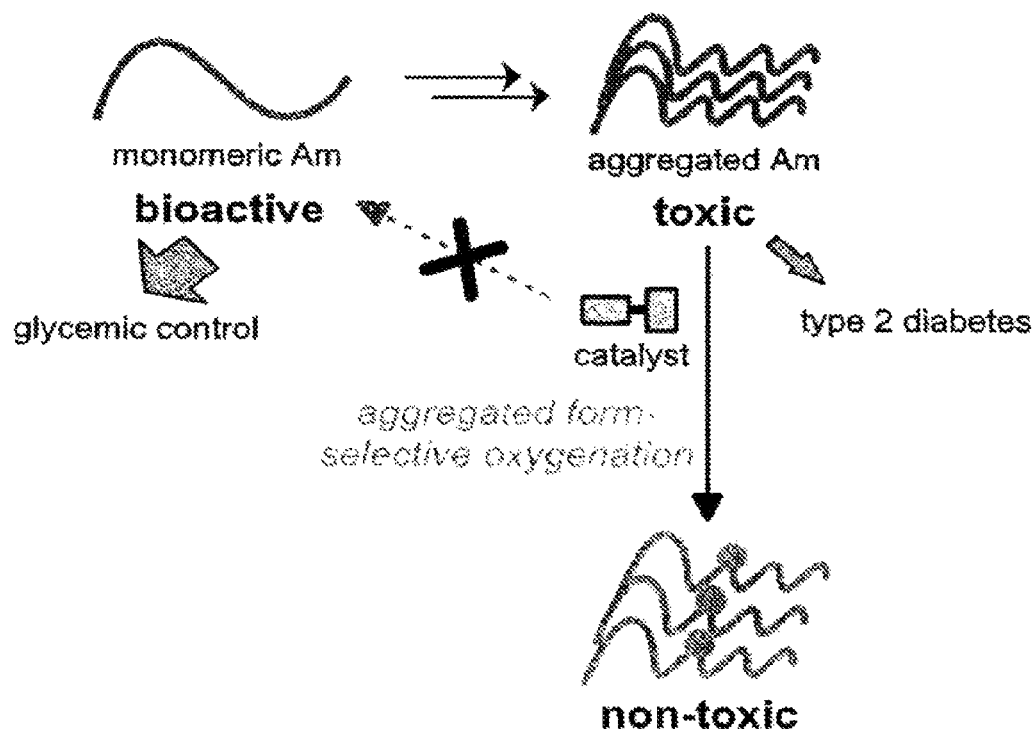

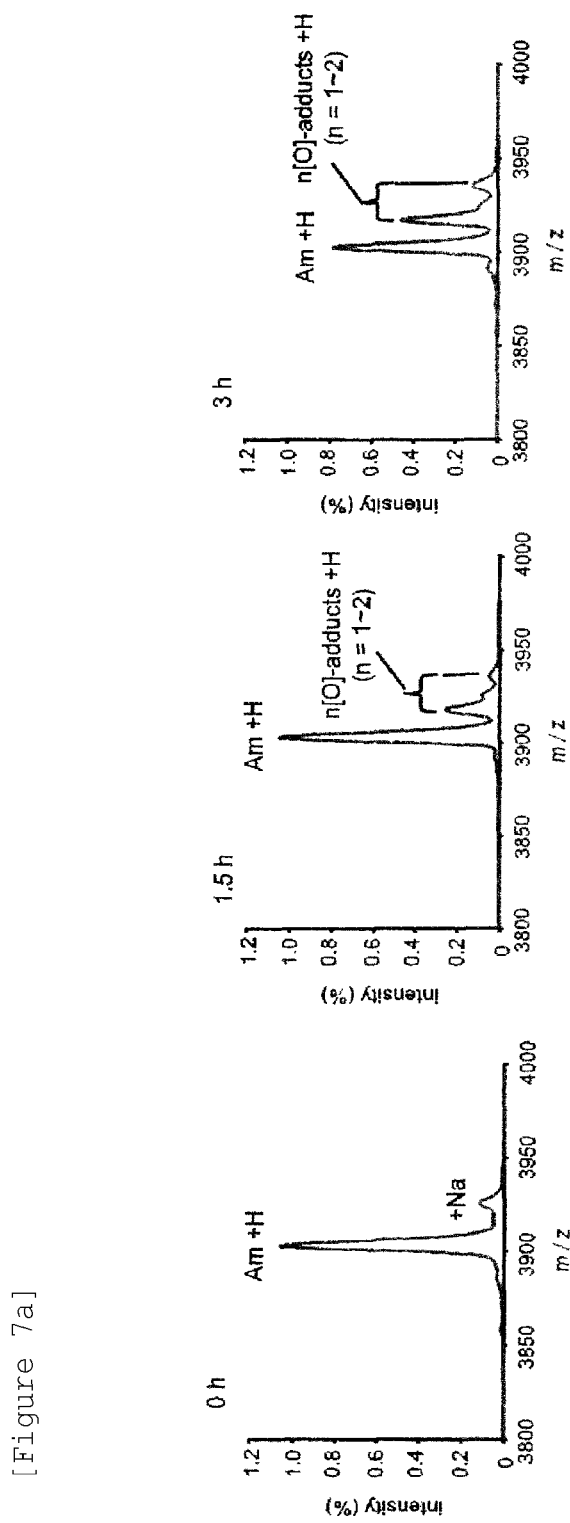
[Figure 7a]

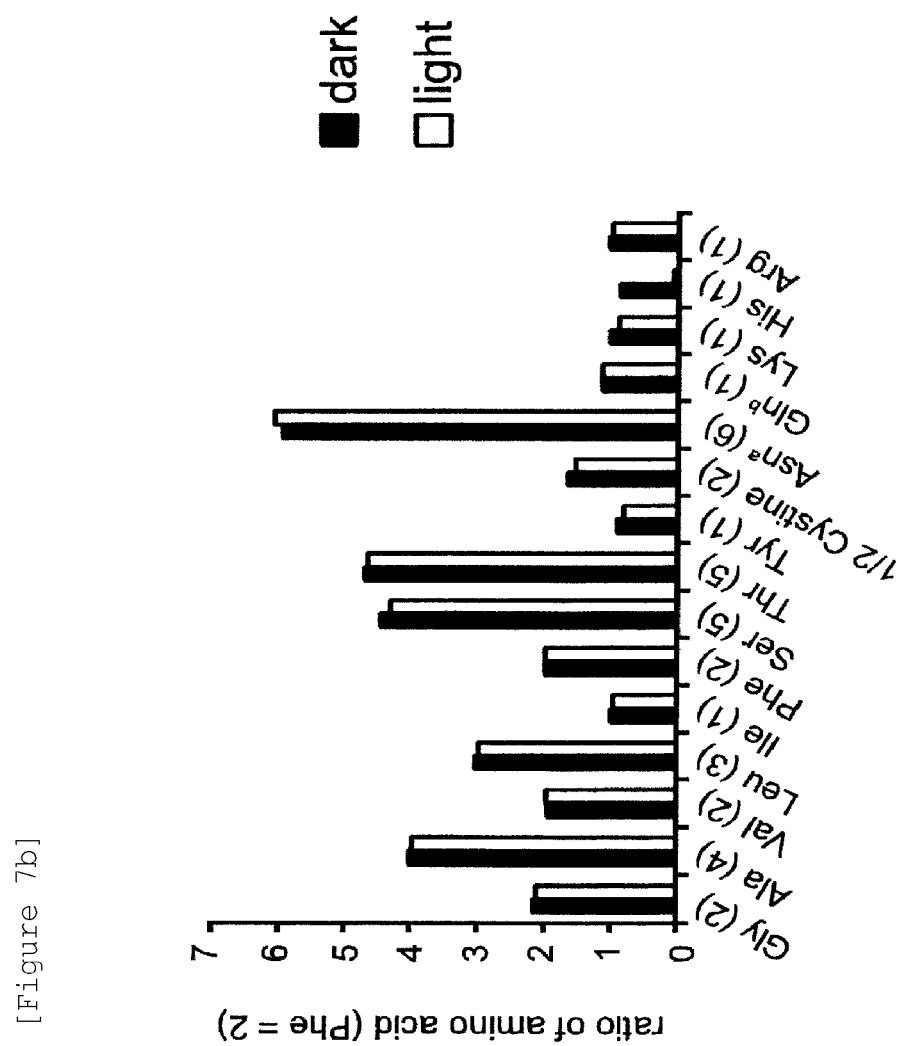
[Figure 7b]

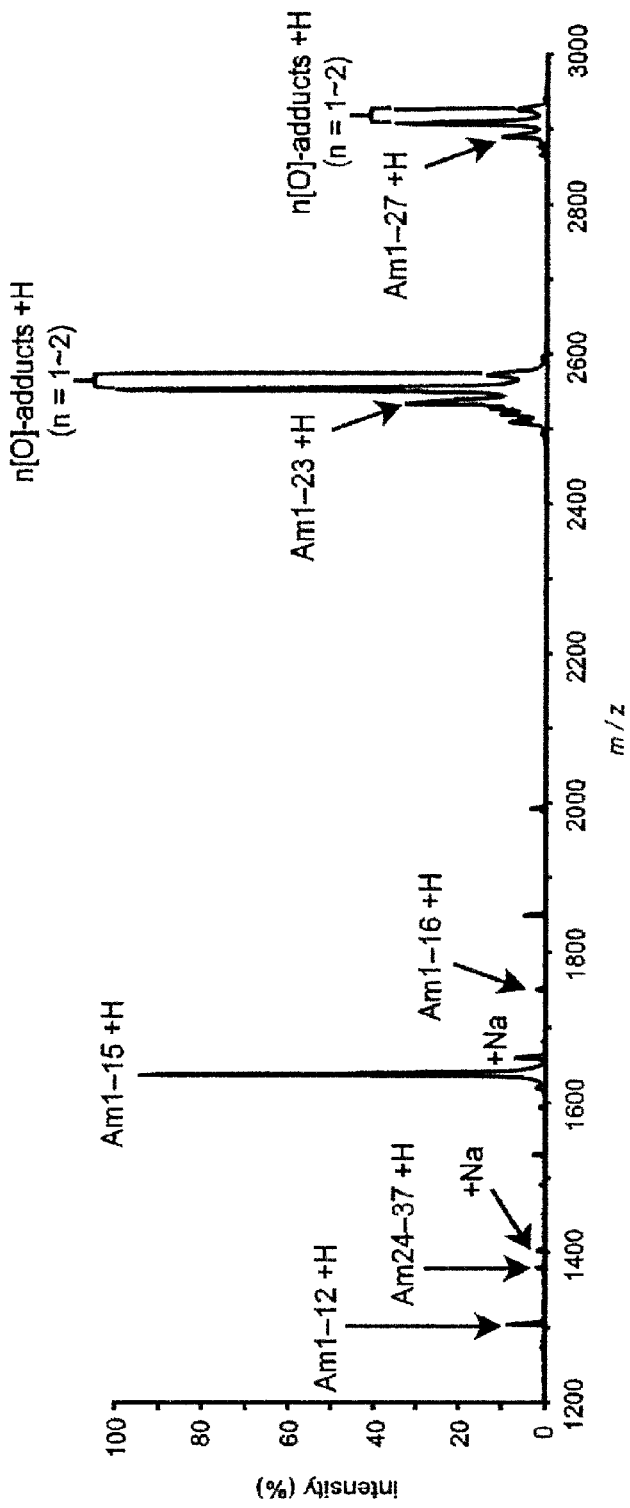
[Figure 7c]

[Figure 8]
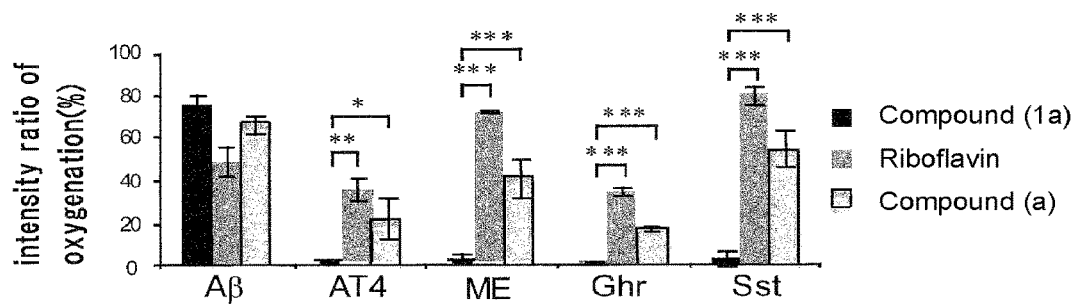

[Figure 9a]
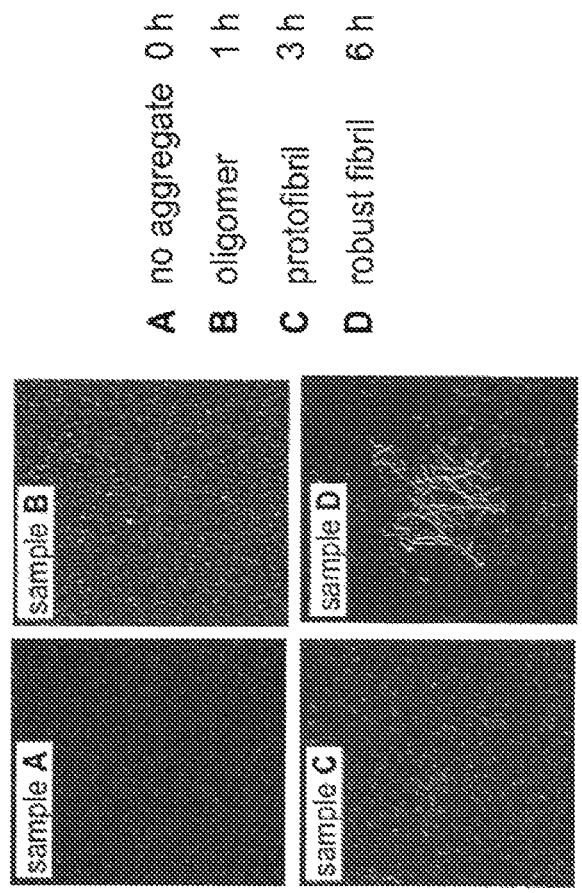

[Figure 9b]
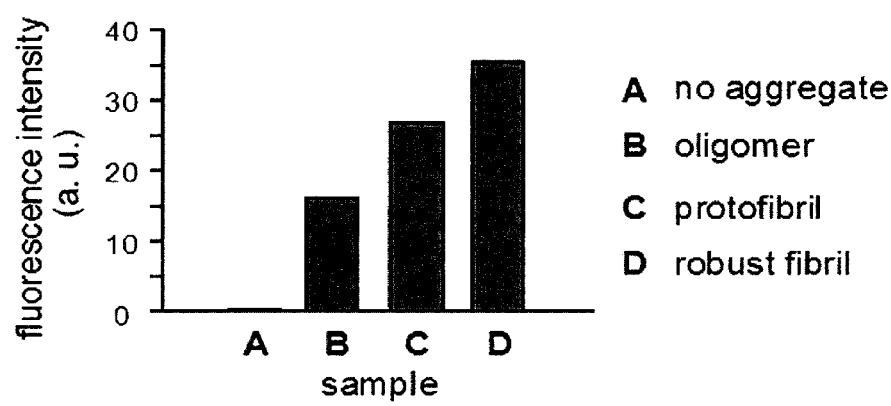

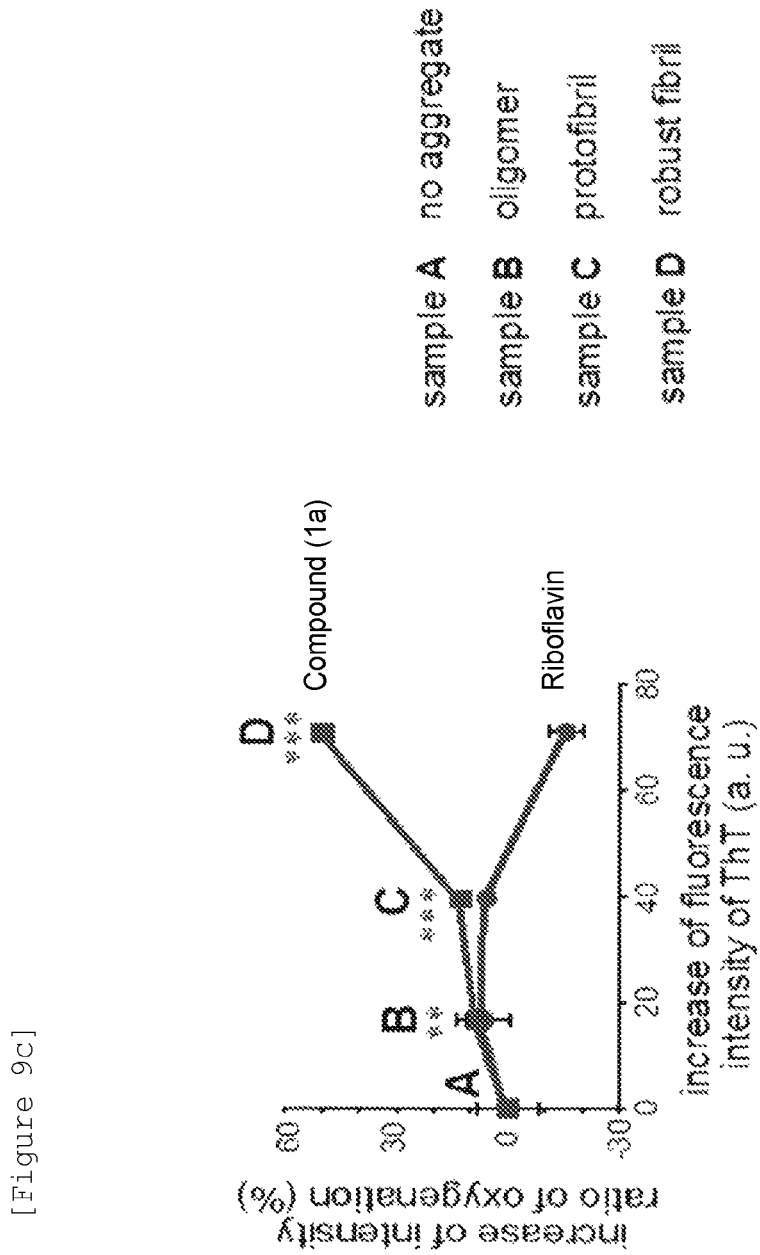
[Figure 9c]

[Figure 10a]
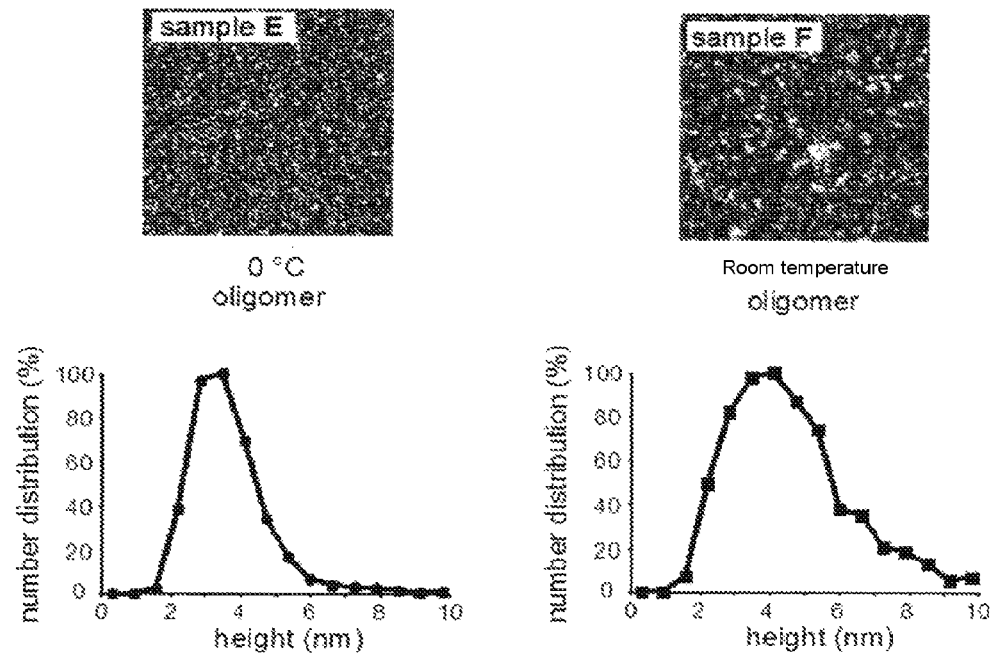
[Figure 10b]
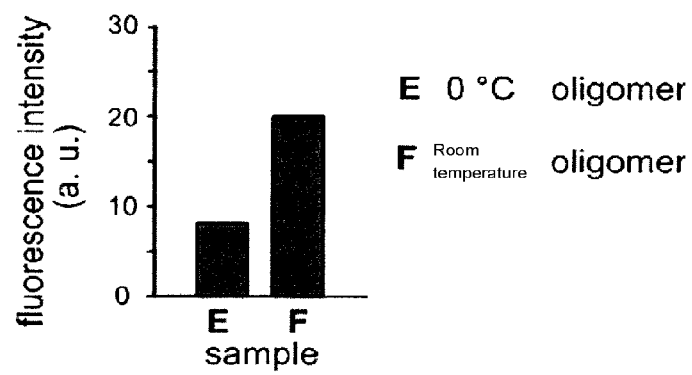
E  0 °C  oligomer
F  Room temperature  oligomer

[Figure 10c]
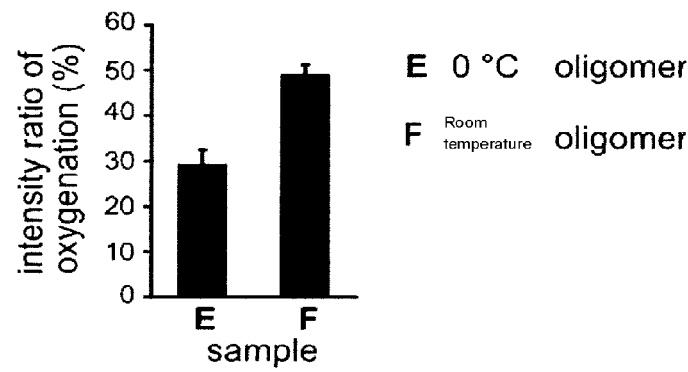
[Figure 10d]
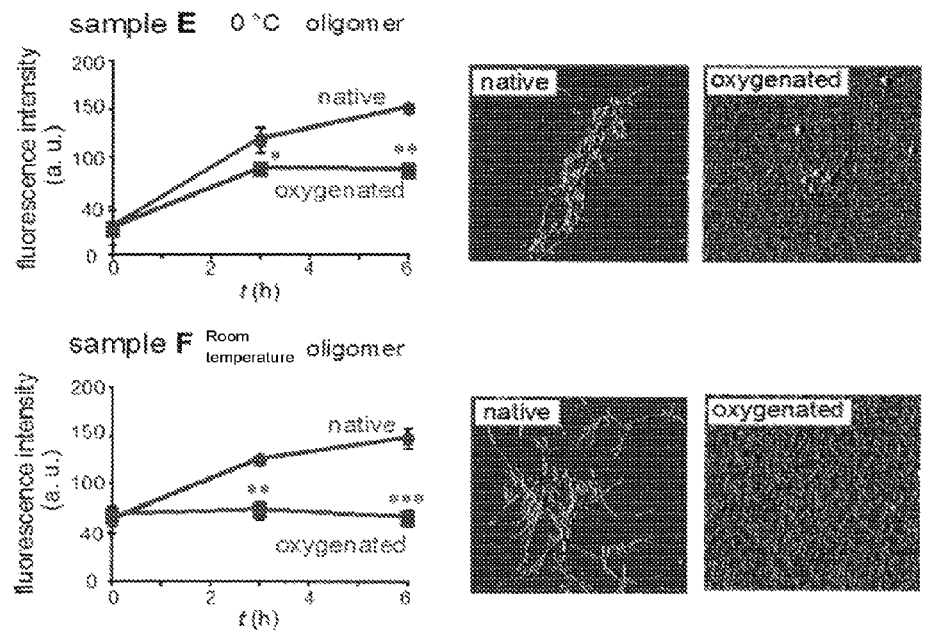

[Figure 11a]
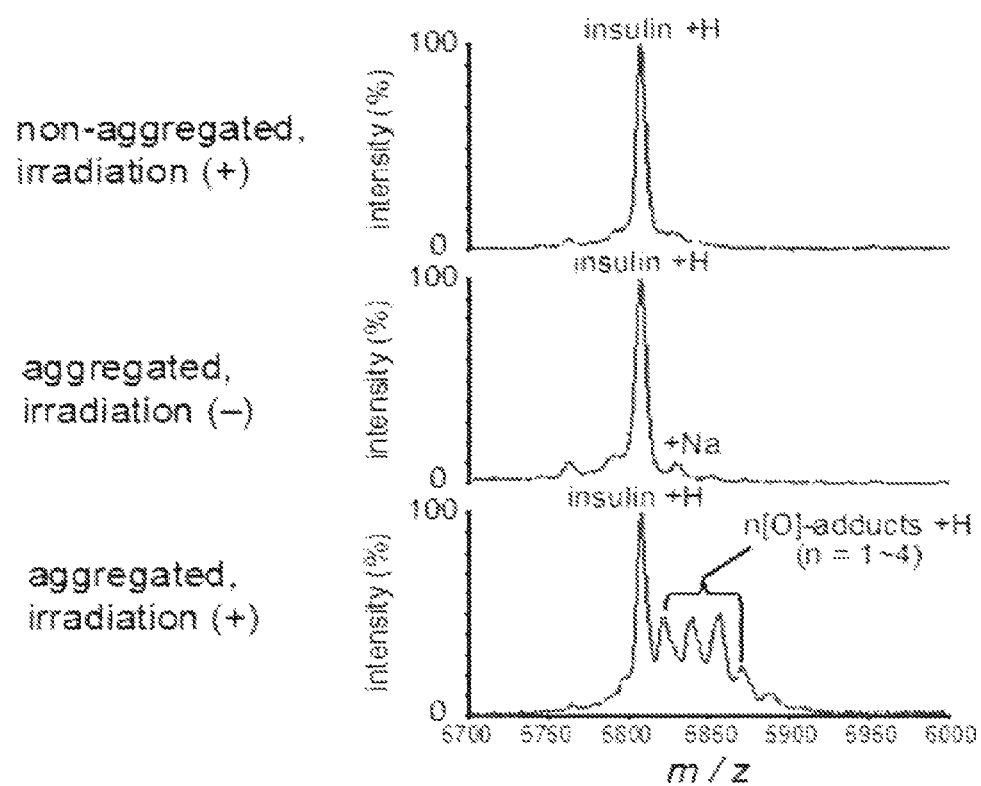

[Figure 11b]
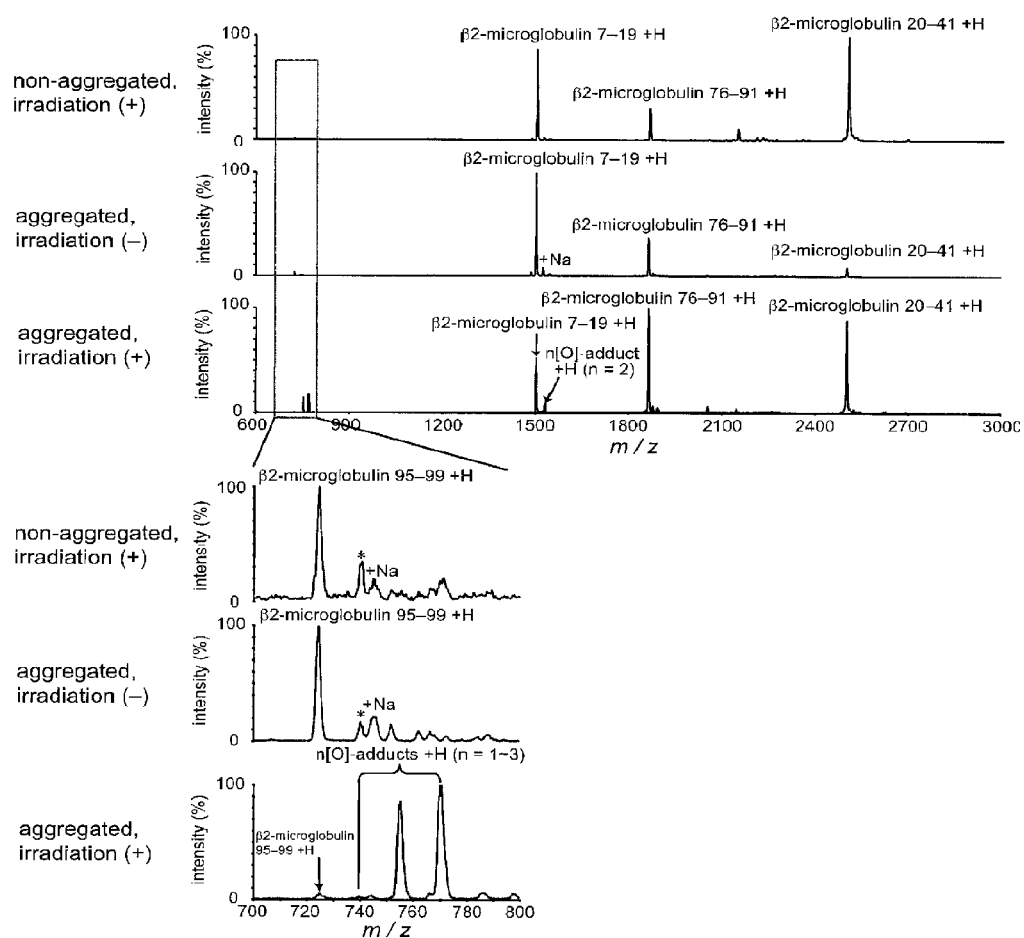

[Figure 11c]
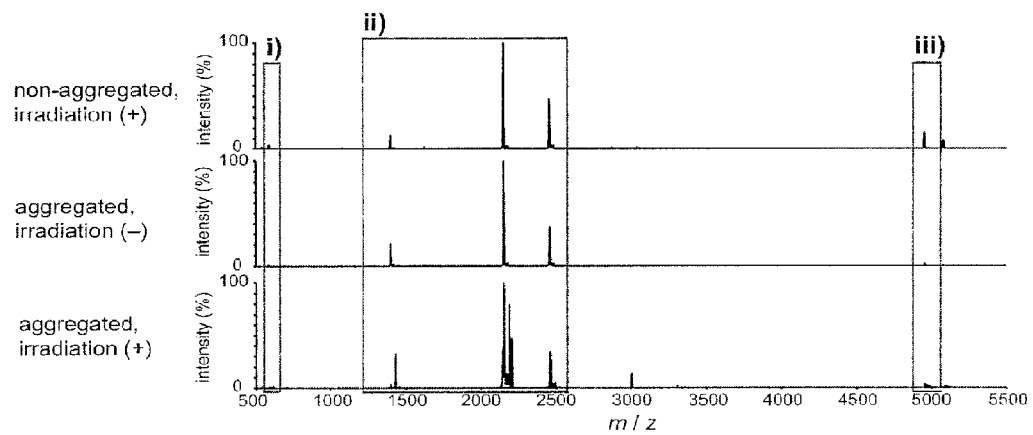

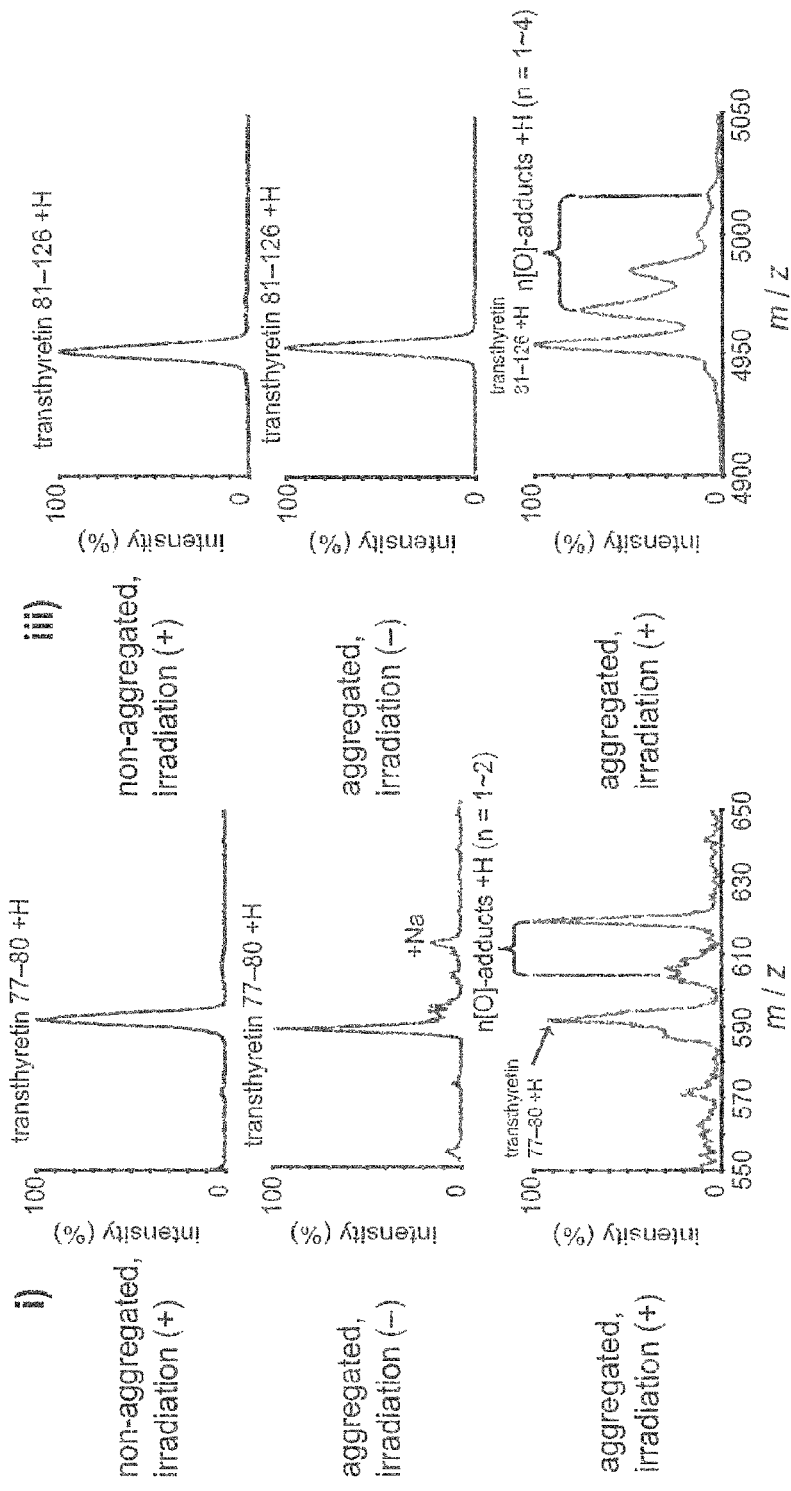
[Figure 11d]

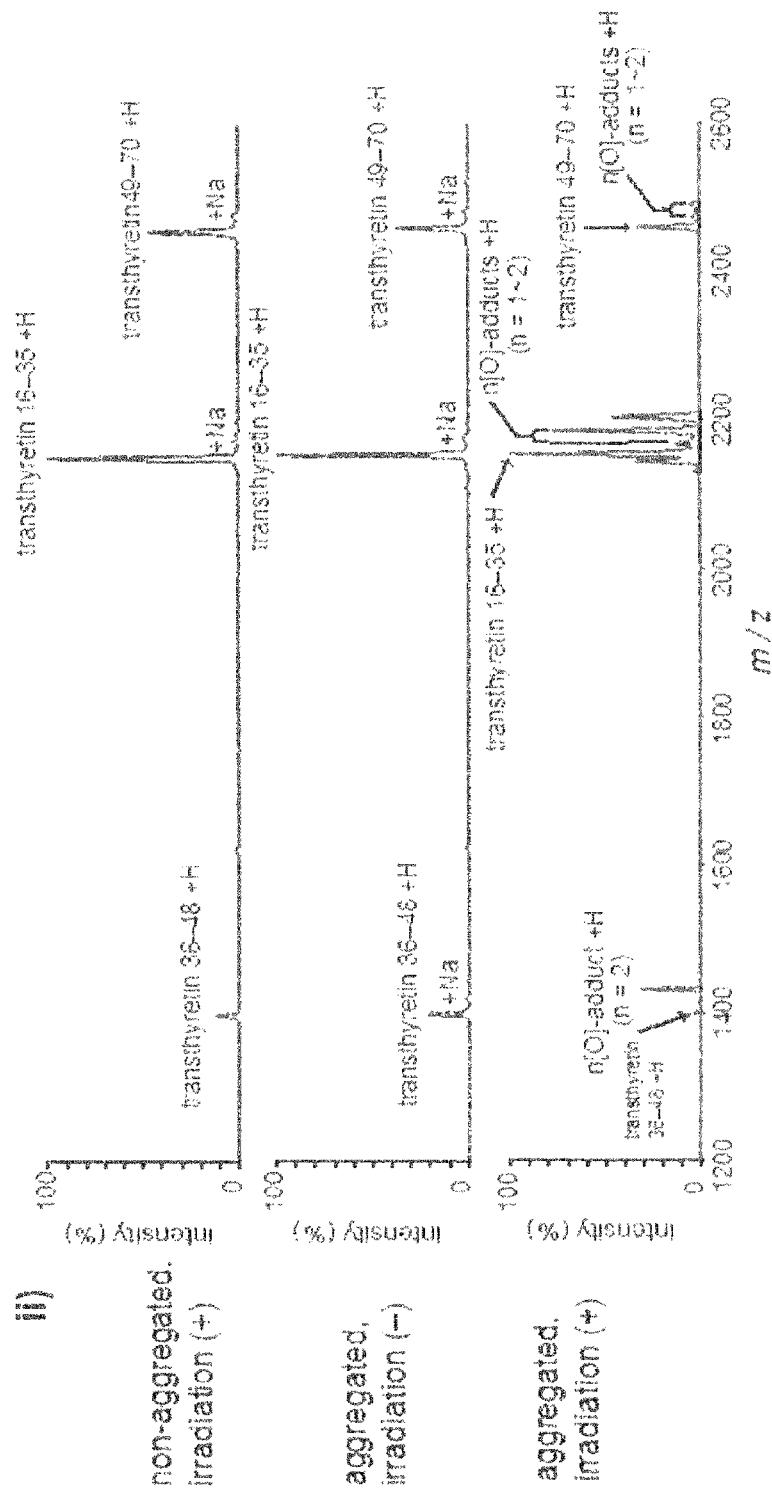
[Figure 11e]

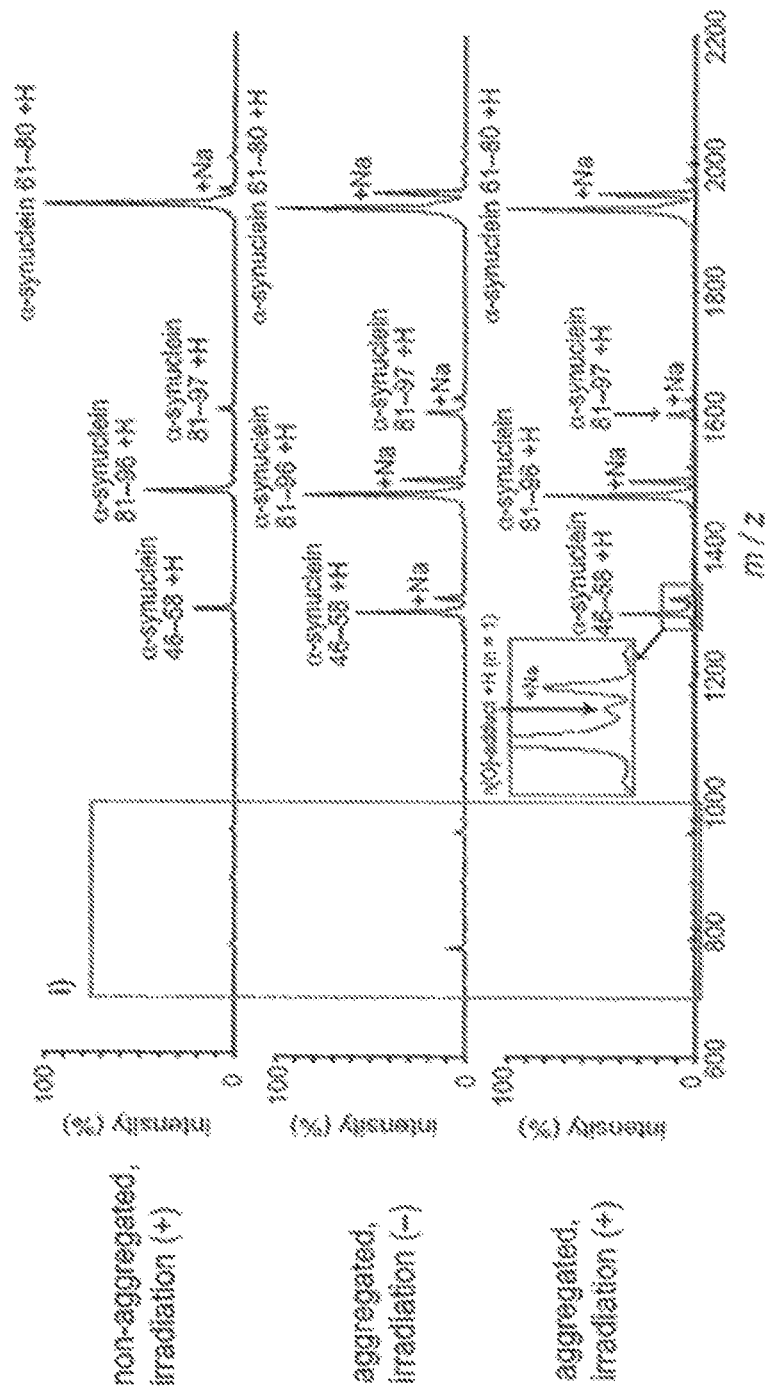
[Figure 11f]

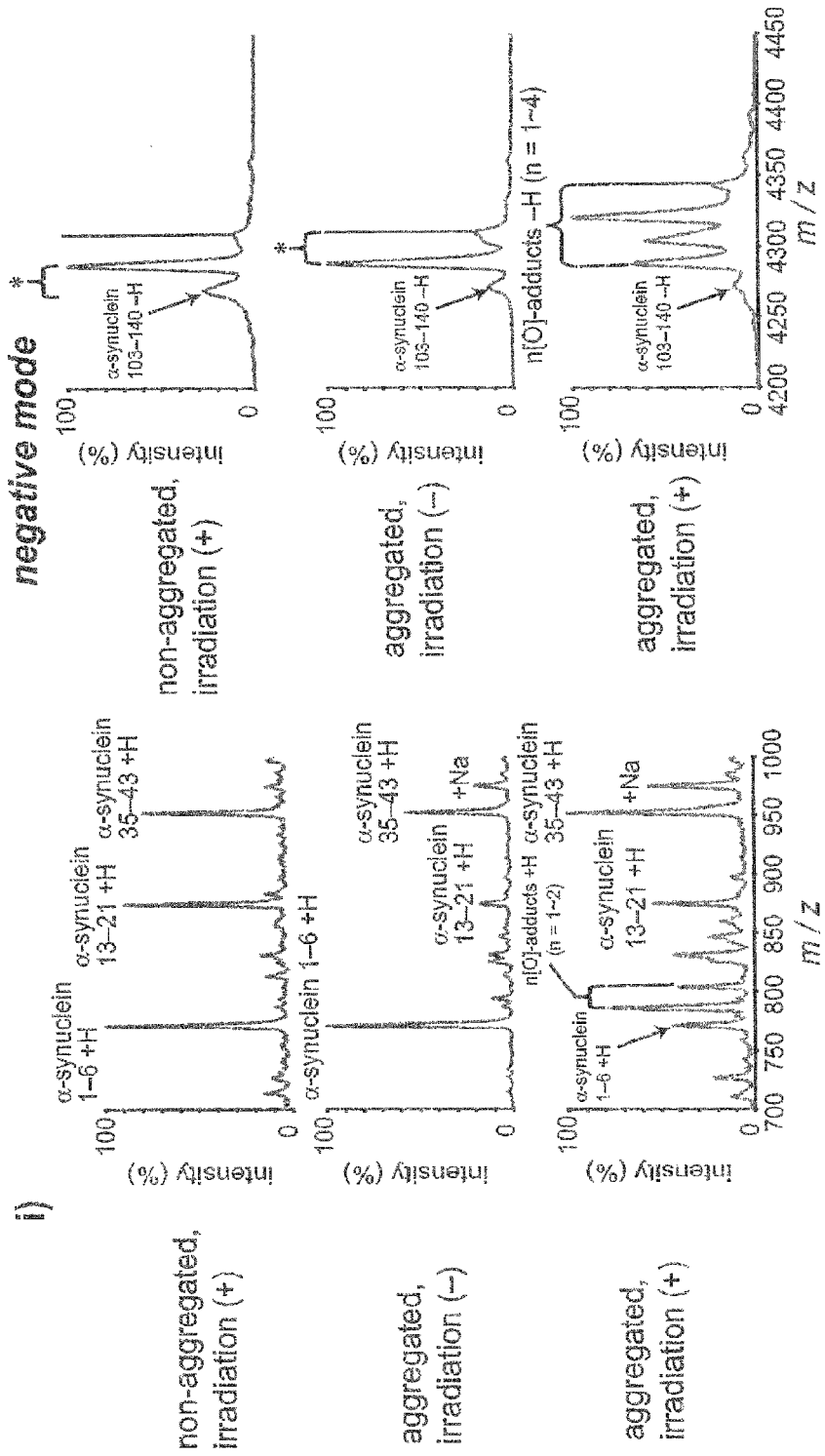
[Figure 11g]

[Figure 12a]
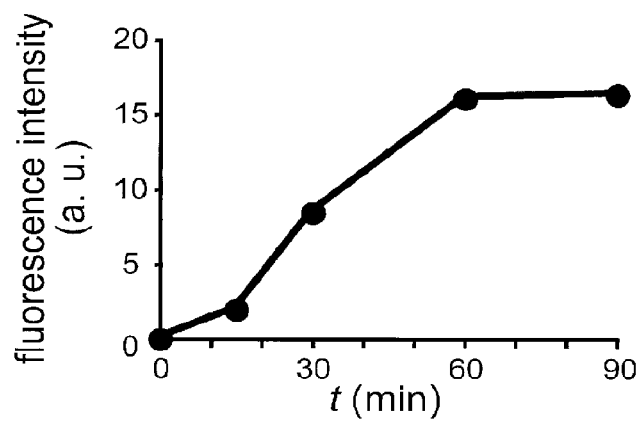
[Figure 12b]
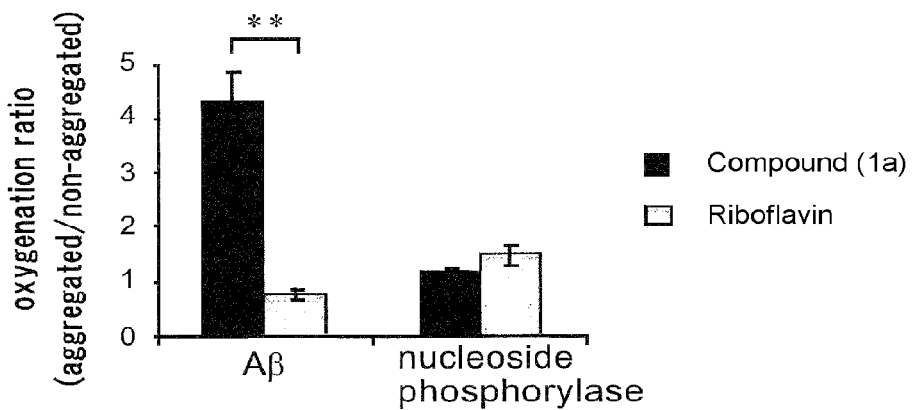

[Figure 13]
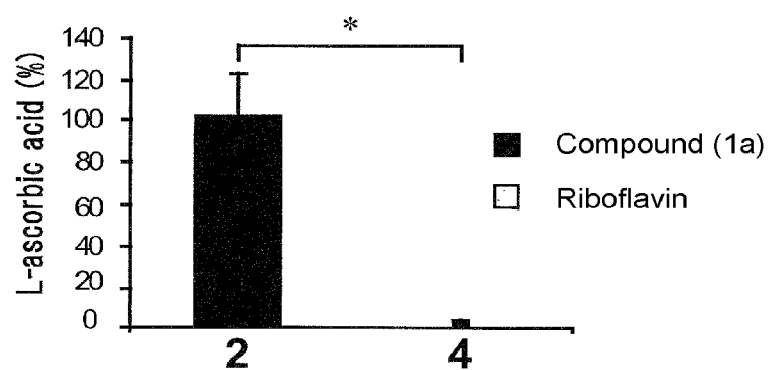

BENZOTHIAZOLE COMPOUND AND MEDICINE CONTAINING SAME

FIELD OF THE INVENTION

The present invention relates to a medicine for the prevention or treatment of diseases involving various amyloids.

BACKGROUND OF THE INVENTION

Proteins are normally responsible for vital functions by forming specific native structures through folding. On the other hand, proteins may be misfolded to undergo aggregation into fibrils (amyloid fibril formation) rich in β-sheet structures. Aggregates (oligomers, protofibrils, and fibrils) produced in the course of this amyloid fibril formation are known to cause various dysfunctions (such diseases are collectively referred to as "amyloid diseases"), and 20 or more types of proteins have been identified as causative agents of the amyloid diseases. For example, amyloid β and Tau protein for Alzheimer's disease, α-synuclein for Parkinson's disease, amylin for diabetes mellitus, transthyretin for systemic amyloidosis, and huntingtin for Huntington's disease are known as such amyloids.

For example, as for amyloid β (abbreviated to Aβ), which is a causative amyloid of Alzheimer's disease, inhibitors of enzymes mediating the production of Aβ from a precursor protein, promoters of Aβ-degrading enzymes, immunotherapy, Aβ aggregation inhibitors, and the like are known as strategies to develop therapeutic drugs targeting these pathogenic amyloids.

On the other hand, it has been reported as to Aβ that a Met-oxidized form of an Aβ peptide (the sulfur atom of the Met residue is oxidized to sulfoxide (—S=O—)) remains in a small amount in vivo, and the Met-oxidized form is less aggregable as compared with the native Aβ peptide (Non Patent Literatures 1 to 3). From these viewpoints, the present inventors reported that oxidized forms of Aβ peptides are obtained by the oxidation of the Aβ peptides using a flavin photocatalyst having an Aβ-binding site represented by the formula (a), and these oxidized forms of Aβ peptides suppress the aggregation of Aβ (Non Patent Literature 4).

CITATION LIST

Non Patent Literature

[Non Patent Literature 1] Hou, L. et al., J. Biol. Chem., 2002, Vol. 277, No. 43, p. 40173-40176

[Non Patent Literature 2] Bitan, G. et al., J. Am. Chem. Soc., 2003, Vol. 125, No. 50, p. 15359-15365

[Non Patent Literature 3] Moskovitz, J. et al., Biochemistry, 2011, 50, p. 10687-10697

[Non Patent Literature 4] A. Taniguchi et al., Angew. Chem. Int. Ed., 2014, 53, 1382-1385

SUMMARY OF THE INVENTION

Technical Problem

The flavin photocatalyst used in Non Patent Literature 4 described above, however, has oxidative activity even in the absence of Aβ. This flavin photocatalyst might therefore react nonspecifically in vivo and has thus been difficult to apply in vivo, though applicable in vitro. In addition, the flavin photocatalyst could be applied only to Aβ peptides.

Thus, an object of the present invention is to provide: a compound useful as an amyloid oxidation catalyst which is applicable in vivo and is applicable not only to Aβ peptides but to other amyloids; and a prophylactic or therapeutic drug for an amyloid-related disease, comprising the same.

Solution to Problem

Accordingly, the present inventors conducted various studies to develop a catalyst which has oxidative activity against amyloids and is applicable in vivo, and consequently completed the present invention by finding that a benzothiazole compound represented by the formula (1) given below is useful as an in vivo catalyst which has strong oxidative activity against Aβ peptides and other amyloids and yields oxidized forms of amyloids having no aggregability.

Specifically, the present invention provides the following [1] to [13]:

[1] A benzothiazole compound represented by the following formula (1):

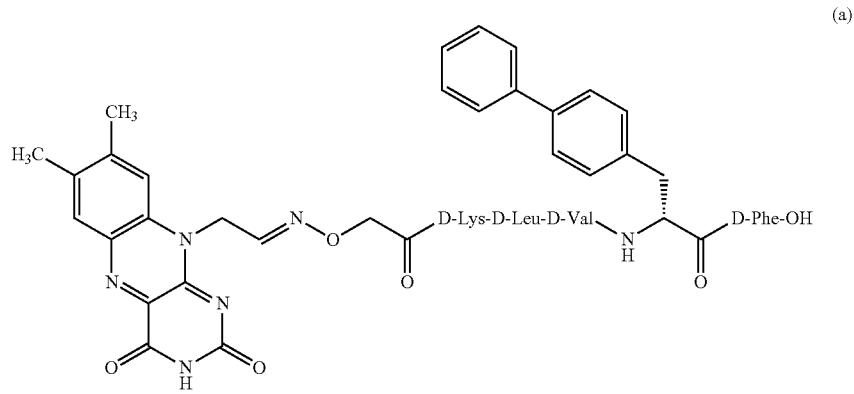

(a)

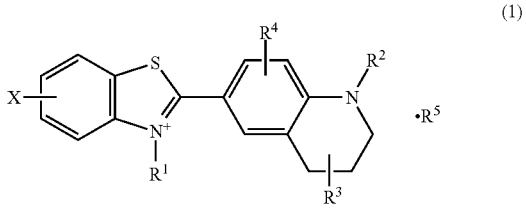

wherein
X represents a halogen atom;
R¹ represents an optionally substituted hydrocarbon group;
R² represents a hydrogen atom or an optionally substituted hydrocarbon group;
R³ and R⁴ are the same or different and each represent a hydrogen atom, an optionally substituted hydrocarbon group, an alkoxy group, a halogen atom, an amino group, a nitro group, or a cyano group;
R² and R⁴ optionally together form an alkylene group; and
$R^n$ represents an anion.

[2] The benzothiazole compound according to [1], wherein the hydrocarbon group represented by each of R¹, R², R³, and R⁴ optionally has 1 to 3 substituents which are the same or different and selected from the group consisting of a halogen atom, an amino group, a nitro group, a cyano group, an alkoxy group, an acyl group, a carboxyl group, an alkoxycarbonyl group, an aromatic hydrocarbon group, and a heterocyclic group.

[3] The benzothiazole compound according to [1] or [2], wherein R¹ is an alkyl or alkenyl group having 1 to 12 carbon atoms.

[4] The benzothiazole compound according to any of [1] to [3], wherein R¹ is an alkyl group having 1 to 12 carbon atoms.

[5] The benzothiazole compound according to any of [1] to [4], wherein R³ is a hydrogen atom or an alkyl or alkenyl group having 1 to 12 carbon atoms.

[6] The benzothiazole compound according to any of [1] to [5], wherein R³ is a hydrogen atom.

[7] The benzothiazole compound according to any of [1] to [6], wherein R² forms a $C_2$-$C_4$ alkylene group together with R⁴, or is an alkyl or alkenyl group having 1 to 12 carbon atoms, the alkyl or alkenyl group optionally having a carboxyl group, an alkoxycarbonyl group, a carbamoyl group, or a dipeptide- to hexapeptide-CO— group, and the carbamoyl group or dipeptide to hexapeptide optionally having 1 or 2 groups selected from the group consisting of a $C_{6-14}$ aryl group and an alkoxycarbonyl group).

[8] A medicine comprising a benzothiazole compound according to any of [1] to [7] as an active ingredient.

[9] The medicine according to [8], wherein the medicine is a prophylactic or therapeutic drug for a disease involving a pathogenic amyloid.

[10] A pharmaceutical composition comprising a benzothiazole compound according to any of [1] to [7] and a pharmaceutically acceptable carrier.

[11] The compound according to any of [1] to [7] for use in the prevention or treatment of a disease involving a pathogenic amyloid.

[12] Use of a compound according to any of [1] to [7] for the production of a prophylactic or therapeutic drug for a disease involving a pathogenic amyloid.

[13] A method for preventing or treating a disease involving a pathogenic amyloid, comprising administering a compound according to any of [1] to [7] to a subject in need thereof.

Effects of Invention

The benzothiazole compound (1) of the present invention has high catalytic activity for the oxidation of pathogenic amyloids such as Aβ peptides and suppresses the aggregation of amyloids by the oxidation of the amyloids in vivo. Thus, the benzothiazole compound (1) of the present invention is useful as a prophylactic or therapeutic drug for a disease involving a pathogenic amyloid.

BRIEF DESCRIPTION OF DRAWINGS

FIG. 1a shows the absorption spectra (left diagrams) and fluorescence spectra (right diagrams) of thioflavin T and compound (1a) in the presence or absence of Aβ1-42. FIG. 1b shows the concentration-fluorescence intensity plots of thioflavin T and compound (1a) in the presence of aggregated Aβ1-42 (prepared by incubation at 37° C. for 3 hours).

FIG. 2a shows analysis on the oxygenation reaction of Aβ1-42 catalyzed by compound (1a) by use of MALDI-TOF MS analysis.

FIG. 2b shows analysis on the oxygenation site of Aβ1-42 by use of amino acid analysis (dark: corresponding to native Aβ, light: corresponding to oxygenized Aβ).

FIG. 2c shows analysis on the oxygenation site of Aβ1-42 using enzymatic digestion with endopeptidase Lys-C. The upper diagram shows the MALDI-TOF MS spectra of a digest mixture, and the lower diagram shows the MS spectra of oxygenated forms of Aβ1-16 fragments in LC/MS/MS.

FIG. 2d shows analysis on the oxygenation site of Aβ1-42 using enzymatic digestion with endopeptidase Lys-C. The MS/MS spectra of Aβ1-16+14 Da derivative (retention time=12.1 and 13.2 min) are shown.

FIG. 3a shows the amino acid sequence of Aβ1-42 (identified oxygenation site is underlined).

FIG. 3b shows the oxygenation reaction of Aβ1-42 catalyzed by thioflavin T or compound (1a).

FIG. 3c shows the oxygenation reaction of Aβ1-42, angiotensin IV, and methionine enkephalin catalyzed by riboflavin, compound (a), or compound (1a).

FIG. 3d shows a putative mechanism underlying Aβ-selective oxygenation by compound (1a).

FIG. 3dA shows the potential energy of compound (1a) in the ground state ($S_0$) and in the excited state ($S_1$) (abscissa: dihedral angle of a benzothiazole site and a julolidine site, ordinate: the lowest energy in the ground state is defined as 0). FIGS. 3dB to 3dD show the fluorescence spectra of compound (1a) in a glycerol/water mixed solvent (B), the reaction of furfuryl alcohol (C), and the reaction of benzoyl methionine (D), respectively.

FIG. 4 shows the aggregability and cytotoxicity of native Aβ1-42 and oxygenized Aβ1-42 (dark: corresponding to native Aβ, light: corresponding to oxygenized Aβ). FIG. 4a shows Nile Red fluorescence assay. FIG. 4b shows atomic force microscopy (incubation time: 6 hr). FIG. 4c shows circular dichroism spectroscopy (incubation time: 6 hr). FIG. 4d shows the evaluation of cell viability using PC12 cells.

FIG. 5 shows analysis on the oxygenation reaction of Aβ1-42 catalyzed by compound (1e) in a cell culture medium (containing 0.1% horse serum) (MALDI-TOF MS spectra are shown).

FIG. 6a shows the amino acid sequence of amylin (identified oxygenation site is indicated by underlined with a line).

FIG. 6b shows the oxygenation reaction of amylin catalyzed by riboflavin or compound (1a) (pre-incubation time=0 h: monomeric state, 1 h: moderately aggregated, 2 h: highly aggregated).

FIG. 6c shows the aggregability of native amylin and oxygenized amylin (Nile Red fluorescence assay).

FIG. 6d shows the aggregability of native amylin and oxygenized amylin (circular dichroism spectroscopy (incubation time: 1 hr) (dark: corresponding to native amylin, light: corresponding to oxygenized amylin).

FIG. 6e shows a schematic diagram of catalytic oxygenation selective for aggregated amylin.

FIG. 7a shows analysis on the oxygenation reaction of amylin catalyzed by compound (1a) by use of MALDI-TOF MS analysis.

FIG. 7b shows analysis on the oxygenation site of amylin by amino acid analysis (dark: corresponding to native amylin, light: corresponding to oxygenized amylin).

FIG. 7c shows analysis on the oxygenation site of amylin using enzymatic digestion with chymotrypsin. The MALDI-TOF MS spectra of an enzymatic digest mixture are shown.

FIG. 8 shows the oxygenation reaction of Aβ1-42, angiotensin IV, methionine enkephalin, desacyl ghrelin, or somatostatin catalyzed by riboflavin, compound (a), or compound (1a).

FIG. 9a shows the cross-β-sheet content analysis of aggregated Aβ1-42 (oligomer and fibril) by use of fluorescence assay and the shape analysis thereof by use of atomic force microscopy.

FIG. 9b shows analysis on the binding of compound (1a) to aggregated Aβ1-42 (oligomer and fibril) by use of fluorescence assay.

FIG. 9c shows increase of the intensity ratio of oxygenation (%) of aggregated Aβ1-42 (oligomer and fibril) by riboflavin and compound (1a) by use of MALDI-TOF MS analysis.

FIG. 10a shows the size distribution analysis of an Aβ1-42 oligomer by use of atomic force microscopy.

FIG. 10b shows analysis on the binding of compound (1a) to an Aβ1-42 oligomer by use of fluorescence assay.

FIG. 10c shows increase of the intensity ratio of oxygenation (%) of an Aβ1-42 oligomer by compound (1a) by use of MALDI-TOF MS analysis.

FIG. 10d shows the aggregability of an oxygenized Aβ1-42 oligomer by compound (1a) using fluorescence assay and an atomic force microscope (compared with non-oxygenized Aβ1-42 (native)).

FIG. 11a shows analysis on the oxygenation reaction of insulin catalyzed by compound (1a) by use of MALDI-TOF MS analysis.

FIG. 11h shows analysis on the oxygenation reaction of β2-microglobulin catalyzed by compound (1a) by use of MALDI-TOF MS analysis.

FIG. 11c shows analysis on the oxygenation reaction of transthyretin catalyzed by compound (1a) by use of MALDI-TOF MS analysis.

FIG. 11d shows analysis on the oxygenation reaction of transthyretin catalyzed by compound (1a) by use of MALDI-TOF MS analysis.

FIG. 11e shows analysis on the oxygenation reaction of transthyretin catalyzed by compound (1a) by use of MALDI-TOF MS analysis.

FIG. 11f shows analysis on the oxygenation reaction of α-synuclein catalyzed by compound (1a) by use of MALDI-TOF MS analysis.

FIG. 11g shows analysis on the oxygenation reaction of α-synuclein catalyzed by compound (1a) by use of MALDI-TOF MS analysis.

FIG. 12a shows the thermal aggregation analysis of nucleoside phosphorylase by use of fluorescence assay.

FIG. 12b shows the oxygenation ratios (%) of aggregated and non-aggregated Aβ1-42 and aggregated and non-aggregated nucleoside phosphorylases by compound (1a) or riboflavin by use of MALDI-TOF MS analysis.

FIG. 13 shows analysis on the oxygenation reaction of L-ascorbic acid catalyzed by compound (1a) or riboflavin by use of MALDI-TOF MS analysis.

DESCRIPTION OF EMBODIMENTS

In the formula (1), X represents a halogen atom. In this context, examples of the halogen atom include a chlorine atom, a bromine atom, a fluorine atom, and an iodine atom. Of them, a chlorine atom or a bromine atom is more preferred, and a bromine atom is further preferred.

$R^1$, $R^2$, $R^3$, and $R^4$ may each represent an optionally substituted hydrocarbon group. In this context, examples of the hydrocarbon group include a linear or branched alkyl group and alkenyl group, a cycloalkyl group, a cycloalkenyl group, and an aromatic hydrocarbon group.

The linear or branched alkyl group or alkenyl group is preferably a linear or branched alkyl group having 1 to 12 carbon atoms or a linear or branched alkenyl group having 2 to 12 carbon atoms, more preferably a linear or branched alkyl group having 1 to 6 carbon atoms or a linear or branched alkenyl group having 2 to 6 carbon atoms. Specific examples of the alkyl group or the alkenyl group include a methyl group, an ethyl group, a n-propyl group, an isopropyl group, a n-butyl group, a n-pentyl group, a n-hexyl group, a vinyl group, and an allyl group.

Examples of the cycloalkyl group or the cycloalkenyl group include a cycloalkyl group having 3 to 8 carbon atoms and a cycloalkenyl group having 3 to 8 carbon atoms. A cycloalkyl group having 3 to 6 carbon atoms or a cycloalkenyl group having 3 to 6 carbon atoms is preferred. Specific examples of the cycloalkyl group or the cycloalkenyl group include a cyclopropyl group, a cyclobutyl group, a cyclopentyl group, and a cyclohexyl group.

The aromatic hydrocarbon group is preferably an aromatic hydrocarbon group having 6 to 14 carbon atoms. Specific examples thereof include a phenyl group, an indenyl group, a naphthyl group, and a biphenyl group.

Of these hydrocarbon groups represented by each of $R^1$ to $R^4$, a linear or branched alkyl group or alkenyl group is preferred, a linear or branched alkyl group is more preferred, a linear or branched alkyl group having 1 to 12 carbon atoms is even more preferred, and a linear or branched alkyl group having 1 to 6 carbon atoms is further preferred.

Examples of the substituent optionally substituted on the hydrocarbon group include 1 to 3 groups selected from the group consisting of a halogen atom, an amino group, a nitro group, a cyano group, an alkoxy group, a carboxyl group, an alkoxycarbonyl group, an acyl group, an aromatic hydrocarbon group, and a heterocyclic group.

In this context, examples of the halogen atom include a fluorine atom, a chlorine atom, a bromine atom, and an iodine atom. Examples of the alkoxy group include an alkoxy group having 1 to 12 carbon atoms. An alkoxy group having 1 to 6 carbon atoms is preferred, and a methoxy group, an ethoxy group, a n-propyloxy group, an isopropyloxy group, a n-butyloxy group, or the like is more preferred. Examples of the alkoxycarbonyl group include a $C_{1-6}$ alkoxycarbonyl group. Examples of the acyl group include an alkanoyl group, an aroyl group, a carboxyalkylcarbonyl group, an alkoxycarbonylalkylcarbonyl group, a carbamoyl group, and a peptide-CO— group and include an alkanoyl group having 1 to 12 carbon atoms, a $C_{6-14}$-aroyl group, a carboxy-$C_{1-12}$ alkylcarbonyl group, a $C_{1-12}$ alkoxycarbonyl-$C_{1-12}$ alkylcarbonyl group, a carbamoyl group, and a dipeptide- to hexapeptide-CO group. The aromatic hydrocarbon group is preferably an aromatic hydrocarbon group having 6 to 14 carbon atoms. Examples thereof include a phenyl group and a naphthyl group. Examples of the heterocyclic group include a 5-membered to 10-membered heterocyclic group having 1 to 3 heteroatoms selected from the group consisting of N, O, and S and specifically include a pyrrolyl group, a thienyl group, a furanyl group, an imidazolyl group, an oxazolyl group, a thiazolyl group, a pyridyl group, and a pyrimidinyl group.

The substituent on each of these hydrocarbon groups is preferably 1 to 3 groups selected from the group consisting of a halogen atom, an amino group, a nitro group, a cyano group, a $C_{1-12}$ alkoxy group, a $C_{1-12}$ alkanoyl group, a $C_{6-14}$ aroyl group, a carboxy-$C_{1-12}$ alkylcarbonyl group, a $C_{1-12}$ alkoxycarbonyl-$C_{1-12}$ alkylcarbonyl group, a carboxyl group, an alkoxycarbonyl group, a carbamoyl group, a dipeptide- to hexapeptide-CO group, a $C_{6-14}$ aryl group, and a 5-membered to 10-membered heterocyclic group having 1 to 3 heteroatoms selected from the group consisting of N, O, and S.

The alkoxy group represented by each of $R^3$ and $R^4$ is preferably an alkoxy group having 1 to 12 carbon atoms, more preferably an alkoxy group having 1 to 6 carbon atoms. Specific examples thereof include a methoxy group, an ethoxy group, a n-propyloxy group, an isopropyloxy group, and a n-butyloxy group.

$R^4$ is preferably an alkyl or alkenyl group having 1 to 12 carbon atoms, a cycloalkyl or cycloalkenyl group having 3 to 8 carbon atoms, or an aromatic hydrocarbon group having 6 to 14 carbon atoms. Also, an alkyl or alkenyl group having 1 to 12 carbon atoms is more preferred, an alkyl group having 1 to 12 carbon atoms is even more preferred, an alkyl group having 1 to 6 carbon atoms is further preferred, and an alkyl group having 1 to 4 carbon atoms is still further preferred.

$R^3$ is preferably a hydrogen atom, an alkyl or alkenyl group having 1 to 12 carbon atoms, a cycloalkyl or cycloalkenyl group having 3 to 8 carbon atoms, or an aromatic hydrocarbon group having 6 to 14 carbon atoms, more preferably a hydrogen atom or an alkyl or alkenyl group having 1 to 12 carbon atoms, even more preferably a hydrogen atom.

$R^2$ is preferably an alkyl or alkenyl group having 1 to 12 carbon atoms, a cycloalkyl or cycloalkenyl group having 3 to 8 carbon atoms, or an aromatic hydrocarbon group having 6 to 14 carbon atoms, more preferably an alkyl or alkenyl group having 1 to 12 carbon atoms, further preferably an alkyl or alkenyl group having 1 to 12 carbon atoms, each of these groups optionally having a substitute. In this context, the substituent is preferably 1 to 3 groups selected from the group consisting of a halogen atom, an amino group, a nitro group, a cyano group, a $C_{1-12}$ alkoxy group, a $C_{1-12}$ alkanoyl group, a $C_{6-14}$ aroyl group, a carboxy-$C_{1-12}$ alkylcarbonyl group, a $C_{1-12}$ alkoxycarbonyl-$C_{1-12}$ alkylcarbonyl group, a carboxyl group, an alkoxycarbonyl group, a carbamoyl group, a dipeptide- to hexapeptide-CO group, a $C_{6-14}$ aryl group, and a 5-membered to 10-membered heterocyclic group having 1 to 3 heteroatoms selected from the group consisting of N, O, and S. The substituent is more preferably a carboxyl group, an alkoxycarbonyl group, a carbamoyl group, or a dipeptide to hexapeptide-CO group. The amino acid or the dipeptide to hexapeptide is optionally substituted by 1 or 2 groups selected from the group consisting of a $C_{6-14}$ aryl group and an alkoxycarbonyl group.

The alkylene group formed by $R^2$ and $R^4$ together is preferably an alkylene group having 2 to 4 carbon atoms. Examples thereof include an ethylene group, a trimethylene group, and a tetramethylene group. When $R^2$ and $R^4$ together form an alkylene group, the substituent $R^4$ is preferably substituted at position 8 on the tetrahydroquinoline ring.

The anion represented by $R^5$ is preferably a halogen anion, a sulfonate anion, or a triflate anion.

In the formula (1), preferably, $R^4$ is an alkyl or alkenyl group having 1 to 12 carbon atoms, a cycloalkyl or cycloalkenyl group having 3 to 8 carbon atoms, or an aromatic hydrocarbon group having 6 to 14 carbon atoms, each optionally having a substituent;

$R^2$ is a hydrogen atom, an alkyl or alkenyl group having 1 to 12 carbon atoms, a cycloalkyl or cycloalkenyl group having 3 to 8 carbon atoms, or an aromatic hydrocarbon group having 6 to 14 carbon atoms, each optionally having a substituent;

$R^3$ and $R^4$ are the same or different and each represent a hydrogen atom, an alkyl or alkenyl group having 1 to 12 carbon atoms, a cycloalkyl or cycloalkenyl group having 3 to 8 carbon atoms, an aromatic hydrocarbon group having 6 to 14 carbon atoms, each optionally having a substituent, an alkoxy group, a halogen atom, an amino group, a nitro group, or a cyano group;

$R^2$ and $R^4$ optionally together form a $C_2$-$C_4$ alkylene group;

$R^5$ is an anion; and the substituent is 1 to 3 groups selected from the group consisting of a halogen atom, an amino group, a nitro group, a cyano group, a carboxyl group, an alkoxycarbonyl group, an alkoxy group, an acyl group, an aromatic hydrocarbon group, and a heterocyclic group.

In the formula (1), more preferably, R is an alkyl or alkenyl group having 1 to 6 carbon atoms, a cycloalkyl or cycloalkenyl group having 3 to 6 carbon atoms, or an aromatic hydrocarbon group having 6 to 14 carbon atoms, each optionally having a substituent;

$R^2$ is a hydrogen atom, an alkyl or alkenyl group having 1 to 6 carbon atoms, a cycloalkyl or cycloalkenyl group having 3 to 6 carbon atoms, or an aromatic hydrocarbon group having 6 to 14 carbon atoms, each optionally having a substituent;

$R^3$ and $R^4$ are the same or different and each represent a hydrogen atom, an alkyl or alkenyl group having 1 to 6 carbon atoms, a cycloalkyl or cycloalkenyl group having 3 to 6 carbon atoms, an aromatic hydrocarbon group having 6 to 14 carbon atoms, each optionally having a substituent, a $C_{1-6}$ alkoxy group, a halogen atom, an amino group, a nitro group, or a cyano group;

$R^2$ and $R^4$ optionally together form a $C_2$-$C_4$ alkylene group;

$R^5$ is an anion; and the substituent is 1 to 3 groups selected from the group consisting of a halogen atom, an amino group, a nitro group, a cyano group, a $C_{1-12}$ alkoxy group, a $C_{1-12}$ alkanoyl group, a $C_{6-14}$ aroyl group, a carboxy-$C_{1-12}$ alkylcarbonyl group, a $C_{1-12}$ alkoxycarbonyl-$C_{1-12}$ alkylcarbonyl group, a carboxyl group, an alkoxycarbonyl group, a carbamoyl group, a dipeptide- to hexapeptide-CO group, a $C_{6-14}$ aryl group, and a 5-membered to 10-membered heterocyclic group having 1 to 3 heteroatoms selected from the group consisting of N, O, and S.

In the formula (1), further preferably, $R^1$ is an alkyl or alkenyl group having 1 to 12 carbon atoms, more preferably an alkyl group having 1 to 12 carbon atoms;

$R^3$ is a hydrogen atom or an alkyl or alkenyl group having 1 to 12 carbon atoms, more preferably a hydrogen atom;

$R^2$ forms a $C_2$-$C_4$ alkylene group together with $R^4$, or is an alkyl or alkenyl group having 1 to 12 carbon atoms (this alkyl or alkenyl group is optionally substituted by a carboxyl group, an alkoxycarbonyl group, a carbamoyl group, or a dipeptide- to hexapeptide-CO group, and this carbamoyl group or dipeptide to hexapeptide is optionally further substituted y 1 or 2 groups selected from the group consisting of a $C_{6-14}$ aryl group and an alkoxycarbonyl group); and $R^5$ is an anion.

When the compound (1) of the present invention has asymmetric carbon atoms, the compound (1) of the present invention has optical isomers. The present invention includes all of optical isomers and racemates.

The compound (1) of the present invention can be produced, for example, according to the following reaction scheme:

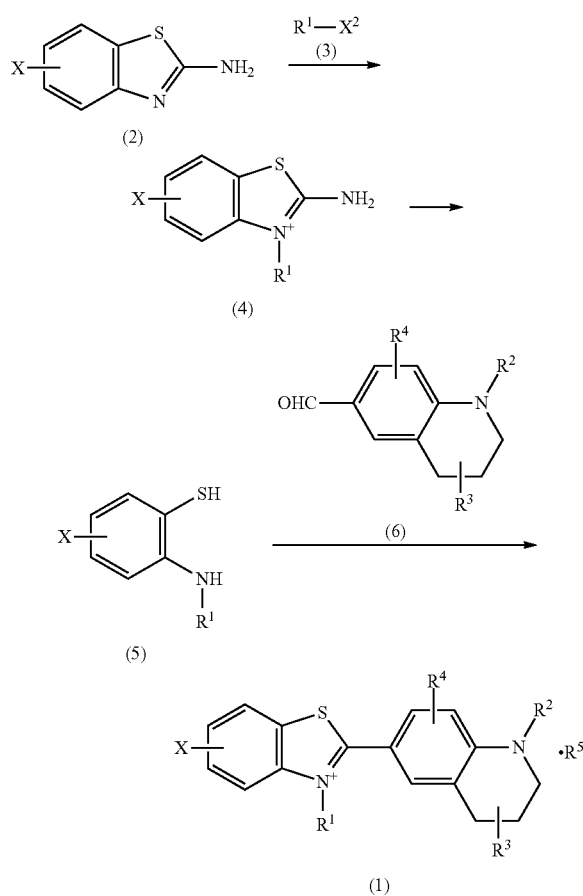

wherein $X^2$ represents an iodine atom, and X and $R^1$ to $R^5$ are as defined above.

2-Aminobenzothiazole (2) is reacted with iodide $R^1$—$X^2$ (3) to obtain quaternary ammonium salt (4). The quaternary ammonium salt is reacted with an alkali to obtain compound (5). Subsequently, the compound (5) is reacted with compound (6) to produce the compound (1) of the present invention.

First, the reaction of the 2-aminobenzothiazole (2) with the iodide (3) can be carried out at room temperature to reflux temperature for 5 minutes to 5 hours in an amide solvent such as dimethylformamide.

Examples of the alkali for use in the reaction of the quaternary ammonium salt (4) can include potassium hydroxide and sodium hydroxide. The reaction of the quaternary ammonium salt (4) with the alkali can be carried out, for example, at room temperature to reflux temperature for 5 hours to 48 hours in a solvent such as ethylene glycol.

The reaction of the compound (5) with the compound (6) is preferably carried out by reacting the compound (5) first with a reducing agent such as tris(2-carboxyethyl)phosphine hydrochloride and subsequently with the compound (6).

The reaction of the compound (5) with the reducing agent can be carried out at room temperature for 10 minutes to 2 hours in a solvent such as water or an alcohol. The reaction of the compound (5) with the compound (6) can be carried out at room temperature to 100° C. for 30 minutes to 12 hours.

The compound (6) can be produced, for example, by the formulation of position 6 of a tetrahydroquinoline through the Vilsmeier-Haack reaction of reacting the tetrahydroquinoline with dimethylformamide and phosphoric acid trichloride.

The substituent on the hydrocarbon group of $R^2$ may be introduced onto the hydrocarbon group of $R^2$ after the reaction of the compound (5) with the compound (6).

The compound (1) of the present invention thus obtained can be isolated and purified from the reaction mixture by an ordinary approach such as washing, crystallization, recrystallization, or chromatography.

The maximum absorption wavelength of the compound (1) of the present invention was shifted to a longer wavelength by approximately 50 nm than that of thioflavin T. The absorption wavelength of the compound (1) of the present invention was observed at a slightly longer wavelength in the presence of Aβ than in the absence of Aβ, while its remarkably high fluorescence was observed. As is evident from these results, the compound of the present invention emits fluorescence as a result of inhibiting intramolecular twisting by binding to Aβ, as with thioflavin T.

When the compound (1) of the present invention was added to Aβ and the mixture was irradiated with light under physiological conditions, native Aβ was decreased over time while oxygenized Aβ in which 1 to 4 oxygen atoms added to Aβ was increased. The oxidation efficiency was remarkably high as compared with thioflavin T. Also, the compound (1) of the present invention has remarkably stronger oxidative activity against Aβ oligomers and Aβ aggregates having a cross-β-sheet structure than its oxidative activity against Aβ1-42 (non-aggregated) and probably suppresses the neurotoxicity of Aβ by the specific oxidation of the cross-β-sheet structures of Aβ oligomers and Aβ aggregates. Furthermore, the oxygenation reaction catalyzed by the compound (1) of the present invention is exceedingly weak against non-amyloid proteins such as angiotensin IV, methionine enkephalin, desacyl ghrelin, and somatostatin and is selective for amyloid proteins. In addition, the oxygenation reaction of amyloids catalyzed by the compound (1) of the present invention was confirmed even in the presence of cells. Thus, the compound (1) of the present invention acts as a catalyst for the selective oxidation of pathogenic amyloids such as Aβ peptides, amylin, transthyretin, α-synuclein, Tau protein, and huntingtin. These pathogenic amyloids, when oxidized, no longer form β-sheet structure layers and therefore become non-pathogenic. Thus, the compound (1) of the present invention is useful as a prophylactic or therapeutic drug for a disease involving a pathogenic amyloid, such as Alzheimer's disease, Parkinson's disease, diabetes mellitus, Huntington's disease, or systemic amyloidosis, in animals including humans.

The compound (1) of the present invention catalyzes the oxidation reaction of a pathogenic amyloid. This oxidation reaction proceeds as the compound (1) of the present invention becomes an excited state by light to cause the oxidation of the amyloid. Thus, in the case of using the compound (1) of the present invention as a medicine, the patient given the compound (1) of the present invention is preferably irradiated with light. The wavelength of the light for causing the excited state of the compound (1) of the present invention is a wavelength as long as 600 to 1200 nm. Therefore, a feature of this wavelength is to easily penetrate living bodies.

Examples of the amino acid residue in an amyloid to be oxidized (oxygenated) by the action of the compound (1) of the present invention include the sulfur atom of a methionine residue and the imidazole ring of a histidine residue.

The pharmaceutical composition comprising the compound (1) of the present invention can be prepared according to various formation methods by selecting an appropriate preparation according to an administration method and using a pharmaceutically acceptable carrier. Examples of the dosage form of the pharmaceutical composition comprising the compound (1) of the present invention as a principal agent can include oral preparations such as tablets, powders, granules, capsules, solutions, syrups, elixirs, and oily or aqueous suspensions.

As for an injection, a stabilizer, an antiseptic, and a solubilizer may be used in the preparation, and a solution optionally containing these auxiliaries may be stored in a container and then prepared by freeze drying or the like into a solid preparation to be prepared when needed. A single dose may be stored in one container, or multiple doses may be stored in one container.

Examples of a preparation for external use can include solutions, suspensions, emulsions, ointments, gels, creams, lotions, sprays, and patches.

The solid preparation contains a pharmaceutically acceptable additive in addition to the compound (1) of the present invention and can be formulated by selecting, for example, fillers, expanders, binders, disintegrants, dissolution promoters, wetting agents, and lubricants if necessary and mixing the selected additives with the compound (1) of the present invention.

Examples of a liquid preparation can include solutions, suspensions, and emulsions. The liquid preparation may contain an additive such as a suspending agent or an emulsifying agent.

In the case of using the compound (1) of the present invention as a medicine for human bodies, the dose is preferably in the range of 1 mg to 1 g, preferably 1 mg to 300 mg, per day in an adult.

EXAMPLES

Hereinafter, the present invention will be specifically described with reference to Examples. However, the scope of the present invention is not intended to be limited by Examples below.

Example 1

(Synthesis of Compound (1a))

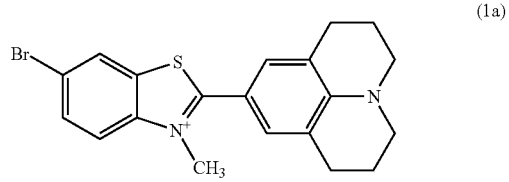 [SMILES: C[n+]1c(-c2cc3c4c(c2)CCCN4CCC3)sc2cc(Br)ccc21]

(1a)

(1) To dimethylformamide (DMF) containing 2-amino-6-bromobenzothiazole (compound (2) in the reaction scheme, 1.39 g, 6.07 mmol) dissolved therein, iodomethane (1.96 mL, 31.48 mmol) was added, and the mixture was stirred at 80° C. for 15 hours. The reaction solution was cooled to room temperature and then diluted with cold diethyl ether, and the suspension was filtered. The obtained deposit was washed with cold diethyl ether and dried under reduced pressure to obtain N-methyl-2-amino-6-bromobenzothiazolium iodine salt (compound (4) in the reaction scheme) (2.19 g, 97%). White solid; $^1$H NMR (400 MHz, DMSO) δ: 10.08 (br, 2H), 8.23 (d, J=2.3 Hz, 1H), 7.76 (dd, J=9.2, 2.3 Hz, 1H), 7.62 (d, J=9.2 Hz, 1H), 3.68 (s, 3H); LRMS (ESI): m/z calcd [M]$^+$ 243.0, found 242.9.

(2) To N-methyl-2-amino-6-bromobenzothiazolium iodine salt (2.19 g, 5.90 mmol), a 10 M aqueous KOH solution (29 mL) and ethylene glycol (7.3 mL) were added, and the mixture was refluxed for 14 hours. The reaction solution was cooled to room temperature and then neutralized with hydrochloric acid, followed by extraction with chloroform. The obtained organic phase was washed with saturated saline, dried over Na$_2$SO$_4$, and dried under reduced pressure to obtain 5-bromo-2-methylamino-thiophenol (compound (5) in the reaction scheme) (1.26 g).

(3) To ethanol (4 mL) containing 5-bromo-2-methylamino-thiophenol (10 mg) dissolved therein, tris(2-carboxyethyl)phosphine hydrochloride (6.6 mg, 0.023 mmol) dissolved in water (20 μL) was added, and the mixture was stirred at room temperature for 30 minutes in an argon atmosphere. 9-Julolidine carboxaldehyde (10.2 mg, 0.051 mmol) was added to the mixed solution, and the mixture was stirred at 80° C. for 2 hours. The reaction solution was cooled to room temperature and then diluted with cold diethyl ether, and the suspension was filtered. The obtained deposit was washed with cold diethyl ether and dried under reduced pressure to obtain compound (1a) (7.5 mg, 37% from 8). Yellow solid; $^1$H NMR (500 MHz, CDCL$_3$) δ: 8.21 (d, J=1.8 Hz, 1H), 8.18 (d, J=9.2 Hz, 1H), 7.83 (dd, J=9.2, 1.8 Hz, 1H), 7.41 (s, 2H), 4.59 (s, 3H), 3.37-3.39 (m, 4H), 2.83-2.85 (m, 4H), 1.97-2.00 (m, 4H); HRMS (ESI): m/z calcd for C$_{20}$H$_{20}$BrN$_2$S$^+$ [M]$^+$ 399.0525, found 399.0511; HPLC: t$_R$=27.8 mins. (YMC-Pack ODS-AM); purity: >95% (HPLC analysis at 230 nm).

Example 2

(Synthesis of Compounds (1b), (1c), (1d), and (1e))

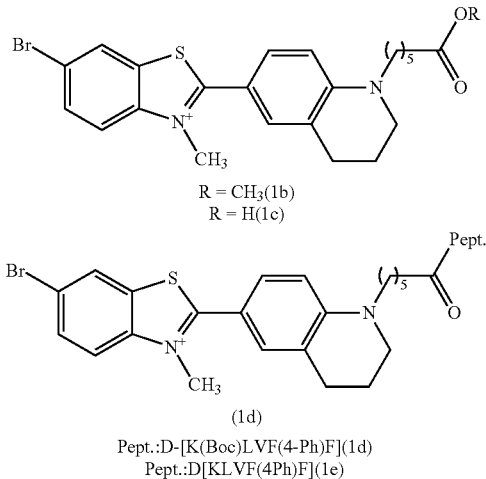

R = CH₃(1b)
R = H(1c)

(1d)
Pept.:D-[K(Boc)LVF(4-Ph)F](1d)
Pept.:D[KLVF(4Ph)F](1e)

(1) 1,2,3,4-Tetrahydroquinoline (0.50 mL, 3.98 mmol) and methyl 6-bromohexanoate (0.76 mL, 4.78 mmol) were added to MeCN (30 mL) containing KI (1.59 g, 9.58 mmol) and $K_2CO_3$ (1.10 g, 7.96 mmol) dissolved therein, and the suspension was stirred at 100° C. for 21 hours in an argon atmosphere. The reaction solution was cooled to room temperature and then diluted with water, followed by extraction with ethyl acetate. The organic phase was washed with saturated saline, dried over $Na_2SO_4$, and dried under reduced pressure. The residue was purified by flash column chromatography (hexane/EtOAc=100/0 to 80/20) to obtain N-methoxycarbonylpentyl-1,2,3,4-tetrahydroquinoline (1.10 g, 100%). Colorless oil; $^1$H NMR (500 MHz, $CDCL_3$) δ: 7.02 (t, J=7.5 Hz, 1H), 6.91 (d, J=7.5 Hz, 1H), 6.51-6.54 (m, 2H), 3.66 (s, 3H), 3.20-3.26 (m, 4H), 2.73 (t, J=6.3 Hz, 2H), 2.31 (t, J=7.5 Hz, 2H), 1.90-1.94 (m, 2H), 1.63-1.69 (m, 2H), 1.56-1.62 (m, 2H), 1.32-1.38 (m, 2H); LRMS (ESI): m/z calcd $[M+H]^+$ 262.2, found 262.0.

(2) To anhydrous dichloromethane (40 mL) containing N-methoxycarbonylpentyl-1,2,3,4-tetrahydroquinoline (1.10 g, 4.2 mmol) dissolved therein, anhydrous DMF (3.3 mL, 42 mmol) and $POCl_3$ (1.3 mL, 14 mmol) were added, and the mixture was stirred at room temperature for 90 minutes in an argon atmosphere. The reaction solution was diluted with water, neutralized with an aqueous NaOH solution, and concentrated under reduced pressure, followed by extraction with ethyl acetate. The organic phase was washed with water, washed with saturated saline, dried over $Na_2SO_4$, and dried under reduced pressure. The residue was purified by flash column chromatography (hexane/EtOAc=75/25 to 55/45) to obtain N-methoxycarbonylpentyl-1,2,3,4-tetrahydroquinoline-6-carboxaldehyde (887.4 mg, 73%). Pale yellow oil; $^1$H NMR (500 MHz, $CDCL_3$) δ: 9.63 (s, 1H), 7.51 (d, J=8.6 Hz, 1H), 7.43 (s, 1H), 6.53 (d, J=8.6 Hz, 1H), 3.65 (s, 3H), 3.35 (t, J=5.8 Hz, 2H), 3.30 (t, J=7.5 Hz, 2H), 2.75 (t, J=6.3 Hz, 2H), 2.32 (t, J=7.5 Hz, 2H), 1.90-1.95 (m, 2H), 1.59-1.70 (m, 4H), 1.33-1.40 (m, 2H); LRMS (ESI): m/z calcd $[M+H]^+$ 290.2, found 290.2.

(3) To 5-bromo-2-methylamino-thiophenol (308.0 mg) in methanol (54 mL), tris(2-carboxyethyl)phosphine hydrochloride (270.0 mg, 0.94 mmol) dissolved in water (1.9 mL) was added, and the mixture was stirred at room temperature for 60 minutes in an argon atmosphere. N-Methoxycarbonylpentyl-1,2,3,4-tetrahydroquinoline-6-carboxaldehyde (340.7 mg, 1.18 mmol) dissolved in methanol (5 mL) was added to the mixed solution, and the mixture was stirred at 70° C. for 7 hours. The reaction solution was cooled to room temperature, then concentrated under reduced pressure, diluted with water, washed with ethyl acetate, and saturated with NaCl, followed by extraction with chloroform. The organic phase was dried over $Na_2SO_4$ and dried under reduced pressure to obtain compound (1b) (288.9 mg).

(4) To methanol (50 mL) containing compound (1b) (288.9 mg) dissolved therein, a 1 M aqueous NaOH solution (8.28 mL) was gradually added in an ice bath, and the mixture was stirred at room temperature for 10 hours. The reaction solution was neutralized with 2 M hydrochloric acid, concentrated under reduced pressure, and saturated with NaCl, followed by extraction with ethyl acetate. The organic phase was dried over $Na_2SO_4$ and dried under reduced pressure. The residue was purified by preparative HPLC (0.1% aqueous TFA/MeCN=80/20 to 30/70, 50 min) to obtain compound (1c) (48.6 mg, 7% from the ester form). Yellow solid; $^1$H NMR (500 MHz, $CDCL_3$) δ: 8.06 (d, J=1.8 Hz, 1H), 7.86 (dd, J=8.6, 1.7 Hz, 1H), 7.80 (d, J=9.2 Hz, 1H), 7.60 (dd, J=9.2, 2.3 Hz, 1H), 7.35 (d, J=2.3 Hz, 1H), 6.75 (d, J=8.6 Hz, 1H), 4.31 (s, 3H), 3.46 (t, J=6.3 Hz, 2H), 3.41 (t, J=7.5 Hz, 2H), 2.81 (t, J=6.3 Hz, 2H), 2.37 (t, J=6.9 Hz, 2H), 1.97-1.99 (m, 2H), 1.65-1.71 (m, 4H), 1.39-1.45 (m, 2H); HRMS (ESI): m/z calcd for $C_{23}H_{26}BrN_2O_2S^+$ $[M]^+$ 473.0893, found 473.0904.

(5) To DMF/DCM (1:1, 4 mL) containing compound (1c) (13.5 mg, 0.023 mmol), N-hydroxysuccinimide (9.6 mg, 0.083 mmol), and 1-ethyl-3-(3-dimethylaminopropyl)carbodiimide hydrochloride (10.6 mg, 0.055 mmol) dissolved therein, triethylamine (15 µL, 0.108 mmol) was added, and the mixture was stirred at room temperature for 4 days. D-[K(Boc)LVF(4-phenyl)F] [TFA salt, 25 mg, 0.027 mmol; obtained by the Fmoc solid-phase peptide synthesis method; MALDI-TOF MS: m/z calcd$[M+Na]^+$ 851.5, found 851.7.] and triethylamine (20 µL, 0.1435 mmol) were added to the mixed solution, and the mixture was stirred at room temperature for 2 days. The reaction solution (compound (1d)) was concentrated under reduced pressure. Then, 4 M HCl in dioxane was added to the residue, and the mixture was stirred at room temperature for 9 hours. The reaction solution was purified by preparative HPLC (0.1% aqueous TFA/MeCN=80/20 to 30/70, 50 min) to obtain compound (1e) (Pept.=D-[KLVF(4-Ph)F (SEQ ID NO: 1)]) (2.0 mg, 6% from the compound (1c)) as TFA salt. Yellow solid; MALD-TOF MS: m/z calcd $[M]^+$ 1185.5, found 1186.7; HPLC: $t_R$=27.7 min (YMC-Pack ODS-AM); purity: >95% (HPLC analysis at 230 nm).

Example 3

(Properties of Compound of Present Invention, Pharmacological Test 1)

A. Method
(1) Oxidation Reaction
To a phosphate buffer solution (10 mM, pH 7.4) containing Aβ1-42 (20 µM), amylin (5 µM), angiotensin IV (30 µM), or methionine enkephalin (30 µM), thioflavin T (20 µM), riboflavin (4 µM), compound a (20 µM), or compound (1a) (20 µM) was added, and the mixture was incubated at 37° C. under irradiation with LED (wavelength: 500 nm).

Then, the reaction was monitored with a mass spectrometer (MALDI-TOF MS) or LC/MS (ESI-Q).

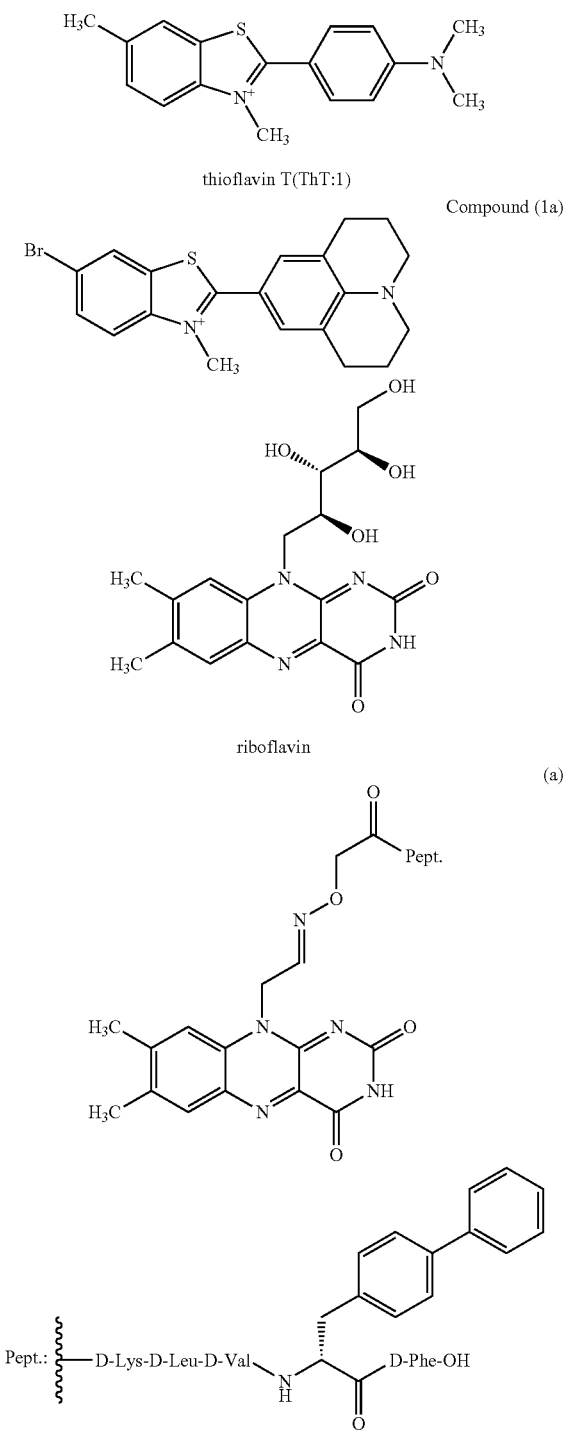

(2) Identification of Oxygenation Site in Aβ1-42 and Amylin

The amino acid analysis of oxidized Aβ1-42 and oxidized amylin (carried out by Peptide Institute, Inc.) was conducted. The oxidized Aβ1-42 and the oxidized amylin were enzymatically digested with endopeptidase Lys-C and chymotrypsin, respectively, and the obtained digests were analyzed with a mass spectrometer (MALD-TOF MS) and LC/MS/MS (ESI-Q-TOF).

(3) Absorption and Fluorescence Spectra

Thioflavin T (20 µM) or compound (1a) (20 µM) was dissolved in the presence or absence of Aβ1-42 (20 µM) in a phosphate buffer solution (10 mM, pH 7.4), and the solution was incubated at 37° C. for 3 hours, followed by the measurement of absorption and fluorescence spectra. The excitation wavelengths for thioflavin T and compound (1a) were set to 420 and 460 nm, respectively.

(4) Aβ Affinity

Aβ1-42 aggregated in advance (aggregation conditions: 20 µM, phosphate buffer solution (10 mM, pH 7.4), 37° C., 3 hr) was added to a phosphate buffer solution (10 mM, pH 7.4) containing thioflavin T or compound (1a) (final concentration of Aβ: 0.5 µM, final concentration of thioflavin T or compound (1a): 0 to 20 µM), and the mixture was incubated at room temperature for 1 hour, followed by the measurement of fluorescence intensity. For thioflavin T, the excitation wavelength was set to 420 nm, and the fluorescence wavelength was set to 485 nm. For compound (1a), the excitation wavelength was set to 460 nm, and the fluorescence wavelength was set to 515 nm. A Kd association curve was obtained from the fluorescence intensity using KaleidaGraph 4.5 (Synergy Software, Reading, Pa.).

(5) Calculation

For thioflavin T and compound (1a), structure optimization and energy calculation at each dihedral angle in the ground state were carried out by DFT calculation using B3LYP/LAV3P* (Maestro 9.3/Jaguar 7.9; Schrodinger, LLC, New York, N.Y., 2012). The energy calculation at each dihedral angle in the excited state was carried out by TDDFT calculation using B3LYP/LAV3P*. The energy in the excited state ($S_1$) was calculated as the sum of the energy in the ground state ($S_0$) and transition energy.

(6) Fluorescence, Singlet Oxygen Production, and Oxidation Reaction in Glycerol/Water Mixed Solvent System To glycerol/water (0:100, 12.5:87.5, 50:50, 62.5:37.5, or 75:25), thioflavin T (20 µM) or compound (1a) (20 µM) was added, followed by the measurement of fluorescence spectra. The excitation wavelengths for thioflavin T and compound (1a) were set to 420 and 460 nm, respectively.

To a solution of furfuryl alcohol (200 µM) or benzoyl methionine (200 µM) dissolved in glycerol/water described above, riboflavin (4 µM) or compound a (20 µM) was added, and the mixture was irradiated with LED (wavelength: 500 nm) at room temperature. Then, the reaction was monitored with LC/MS (ESI-Q).

(7) Experiment of Nile Red Fluorescence Assay

To a phosphate buffer solution (10 mM, pH 7.4) containing Aβ1-42 (20 µM) or amylin (5 µM) dissolved therein, compound (1a) (20 µM) was added, and the mixture was incubated at 37° C. under irradiation with LED (wavelength: 500 nm). A portion of the solution was added to a phosphate buffer solution (10 mM, pH 7.4) containing Nile Red (final concentration of Aβ1-42 or amylin: 0.5 µM, final concentration of Nile Red: 5 µM), and the mixture was incubated at room temperature for 1 hour, followed by the measurement of the fluorescence Intensity of Nile Red (excitation wavelength: 530 nm, fluorescence wavelength: 610 nm).

(8) Experiment of Atomic Force Microscopy

To a phosphate buffer solution (10 mM, pH 7.4) containing Aβ1-42 (20 µM) dissolved therein, compound (1a) (20 µM) was added, and the mixture was incubated at 37° C. under irradiation with LED (wavelength: 500 nm). A portion of the solution was placed on mica, incubated at room temperature for 3 minutes, then washed with water (20 µL), and dried in air. The measurement was carried out using Nano Wizard II (JPK instruments AG, Berlin, Germany) in the tapping mode at room temperature in air.

(9) Experiment of Circular Dichroism Spectroscopy

To a phosphate buffer solution (10 mM, pH 7.4) containing Aβ1-42 (20 µM) or amylin (5 µM) dissolved therein, compound (1a) (20 µM) was added, and the mixture was incubated at 37° C. under irradiation with LED (wavelength: 500 nm). A portion of the solution was analyzed using Model 202SF (AVIV Biomedical, Inc., Lakewood, N.J.).

(10) Cell Experiment

To a Dulbecco's modified eagle's medium containing 0.1% horse serum in which Aβ1-42 (20 µM) was dissolved, compound (1e) (10 µM) was added, and the mixture was incubated at 37° C. for 30 minutes under irradiation with LED (wavelength: 500 nm). Then, the reaction was monitored with a mass spectrometer (MALDI-TOF MS).

The solution was added at 50 µL/well to rat adrenal medulla-derived pheochromocytoma PC12 cells (purchased from RIKEN, Japan) inoculated to a poly-D-lysine-coated 96-well plate and similarly reacted. The reaction solution in each well was diluted with 50 µL of a Dulbecco's modified eagle's medium containing 0.1% horse serum (final concentration of Aβ: 10 µM) and then incubated at 37° C. for 48 hours in a 5% $CO_2$ atmosphere. A live cell count measurement reagent SF containing WST-8 (10 µL; purchased from Nacalai Tesque, Inc.) was added to each well, and the mixture was incubated at 37° C. for 3 hours in a 5% $CO_2$ atmosphere. Then, the cell viability was measured from absorbance at 450 nm (reference wavelength: 655 nm).

B. Results (1) The maximum absorption wavelength (456 nm) of the synthesized compound (1a) was shifted to a longer wavelength by approximately 50 nm than that of thioflavin T due to the stronger electron-donating properties of julolidine (FIG. 1a, left). The absorption wavelength of the compound (1a) was observed at a slightly longer wavelength in the presence of Aβ than in the absence of Aβ, while the fluorescence in the presence of Aβ was remarkably high as compared with that in the absence of Aβ (FIG. 1a). These results suggested that the compound (1a) emits fluorescence as a result of inhibiting intramolecular twisting by binding to Aβ, as with thioflavin T. The association curve based on the fluorescence intensity also revealed that the compound (1a) has the same level of a Kd value as that of thioflavin T (1: 2.9 µM, 4: 1.1 µM) for Aβ (FIG. 1b).

Next, compound (1a) (100 mmol %) was added to Aβ, and the mixture was irradiated with light (wavelength: 500 nm) under physiological conditions (pH 7.4, 37° C.). As a result, native Aβ was decreased over time while oxygenized Aβ in which 1 to 4 oxygen atoms was added to Aβ was increased (FIG. 2a). The oxidation efficiency of Aβ by compound (1a) was remarkably high as compared with thioflavin T (FIG. 3b). As a result of amino acid analysis and LC/MS/MS analysis, it was found as to the oxygenation reaction by compound (1a) that oxygenation proceeds remarkably at His-13 and His-14 residues, and oxygenation also proceeds slightly at Met-35 residue (FIGS. 2a to 2d and 3a). Unlike oxygenation using riboflavin, oxidation at Tyr-10 residue was not observed.

(2) Next, the Aβ selectivity of oxygenation reaction was studied (FIG. 3c). Riboflavin (20 mmol %), compound a (100 mmol %), and compound (1a) (100 mmol %) caused the oxygenation of Aβ at the same level (65 to 70°) under light irradiation conditions of 1.5 hours in a neutral buffer solution (37° C.). On the other hand, under the same conditions as above, riboflavin and compound a caused approximately 40% and 60% oxygenation of angiotensin IV (VYIHPF (SEQ ID NO: 2)) and methionine enkephalin (YGGFM (SEQ ID NO: 3)), respectively (His and Tyr residues in angiotensin I and Met and Tyr residues in methionine enkephalin were oxygenated), whereas the generation of an oxygenated form in each reaction using compound (1a) was reduced to 5% or less. These results suggested that riboflavin and compound (a) catalyzes the oxygenation of various substrates, regardless of amyloid or non-amyloid proteins, whereas the compound (1a) rarely has oxidative activity against ordinary substrates, but selectively catalyzes the oxygenation of amyloid molecules. Under reaction conditions involving Aβ coexisting with angiotensin IV and methionine enkephalin, riboflavin and compound (a) also nonselectively catalyzed the oxygenation of all substrates, whereas the highly selective oxygenation of Aβ was observed in the use of the compound (1a) (FIG. 3c).

The reason for exerting such high amyloid selectivity simulates the mechanism of FIG. 3d based on TICT and intersystem crossing. Specifically, when the compound (1a) is excited into the $S_1$ state by light absorption (FIG. 1a, left), this state is brought back to the ground state ($S_0$ state) via intramolecular rotation (twisted intramolecular charge transfer: TICT) to the $S_1'$ state, in the absence of Aβ. In actuality, potential energy in the ground state and in the excited state was calculated on the basis of computational science as to the dihedral angle of a benzothiazole site and a julolidine site (FIG. 3dA). As a result, the highest stability was attained at approximately 30 degrees in the ground state, whereas the highest stability was attained at approximately 90 degrees in the excited state, suggesting that the $S_1$ state (dihedral angle: approximately 30 degrees) immediately after excitation voluntarily causes intramolecular twisting to the $S_1'$ state (dihedral angle: approximately 90 degrees). The energy gap between the $S_1'$ state and the $S_0'$ state was small at 90 degrees, suggesting that the $S_1'$ state is easily relaxed into the ground state ($S_0'$ state). On the other hand, it is considered that, in the presence of Aβ, binding to Aβ (FIG. 1b) probably inhibits the intramolecular rotation so that TICT does not occur. In the glycerol/water mixed solvent, the fluorescence intensity of the compound (1a) was increased with increase in the concentration of highly viscous glycerol. This also experimentally supported the suppression of TICT by reduction in the intramolecular rotational movement of the compound (1a) (FIG. 3dB). When TICT does not occur, it is considered that a portion of the $S_1$ state causes transition to the $T_1$ state (intersystem crossing), and the $T_1$ state converts molecular oxygen to singlet oxygen. As a result of irradiating the aqueous solution containing glycerol with light in the presence of compound (1a) and furfuryl alcohol (known to react specifically with singlet oxygen), decrease in furfuryl alcohol, i.e., production of singlet oxygen, with increase in the concentration of glycerol was observed (glycerol was confirmed not to participate in the singlet oxygen production by a control experiment) (FIG. 3dC). Benzoyl methionine was further confirmed to be oxidized in a glycerol concentration-dependent manner under similar reaction conditions (glycerol was confirmed not to accelerate the oxidation reaction by a control experiment) (FIG. 3dD).

From the results described above, it is considered that TICT proceeded in the absence of Aβ so that oxygenation did not occur, whereas the intersystem crossing from the $S_1$ state to the $T_1$ state proceeded upon binding to Aβ so that the production of singlet oxygen by the $T_1$ state and the subsequent oxygenation of Aβ by the singlet oxygen proceeded, resulting in the achievement of high Aβ-selective oxygenation (FIG. 3d).

(3) The aggregability of this oxygenized Aβ was further found to be remarkably lower than that of native Aβ. Specifically, as a result of incubation under physiological conditions (pH 7.4, 37° C.) and each of time-dependent Nile Red fluorescence assay (degree and correlation of aggregation) (FIG. 4a), atomic force microscopy (FIG. 4b), and circular dichroism spectroscopy (FIG. 4c), elevation of fluorescence intensity, fibril formation, and change in secondary structure to β-sheet due to aggregation were observed in native Aβ, whereas almost no change was observed in oxygenized Aβ. These results indicated that the aggregability of Aβ is significantly reduced by the oxygenation of any of His-13, His-14, and Met-35 residues (D. A. Butterfield, D. Boyd Kimball, Biochim. Biophys. Acta Proteins Proteomics 2004, 1703, 149-156).

(4) Next, Aβ oxygenation was studied in the presence of cells. Compound (1e) was designed in which the julolidine structure of compound (1a) was replaced with a 1,2,3,4-tetrahydroquinoline structure and the resultant was further bound to an Aβ-affinity peptide D-[Lys-Leu-Val-Phe(4-phenyl)-Phe] (A. Taniguchi, D. Sasaki, A. Shiohara, T. Iwatsubo, T. Tomita, Y. Sohma, M. Kanai, Angew. Chem. Int. Ed., 2014, 53, 1382-1385) via N-alkyl linker. The compound (1e) (50 mmol %) had the activity of oxygenating approximately 40% of Aβ by light irradiation (wavelength: 500 nm) for 30 minutes in a cell medium (FIG. 5). Compound a was able to rarely oxygenate Aβ under the same conditions as above involving a medium (A. Taniguchi, D. Sasaki, A. Shiohara, T. Iwatsubo, T. Tomita, Y. Sohma, M. Kanai, Angew. Chem. Int. Ed., 2014, 53, 1382-1385), whereas the compound (1e) was probably able to efficiently oxygenate Aβ without being interfered with components in the medium, because of producing singlet oxygen nearer to Aβ. Oxygenation reaction was carried out in the presence of cells, and the cell viability was examined after incubation for 2 days. As a result, no phototoxicity of the compound (1e) was observed (FIG. 4d, F). This seems to be derived from the property of lacking the oxidative activity in the absence of Aβ. On the other hand, in the presence of Aβ (comparison between G and H in FIG. 4d), light irradiation significantly elevated the cell viability as compared with no light. This is probably because the toxicity of Aβ was reduced through oxygenation reaction and therefore, cell death was avoided.

(5) Proteins that undergo amyloid fibril formation by misfolding also play physiological roles by the original normal folding in most cases. For example, amylin, a hormone essential for glycemic control, is involved in the destruction of pancreatic β cells and the development of diabetes mellitus by amyloid fibril formation. Thus, for modifying the oxygenation of a pathogenic amyloid, it is important to have no influence on functional proteins responsible for physiological functions. On the other hand, this oxygenation catalyst strategy based on the mechanism of TICT and intersystem crossing induces oxidative activity by binding to the β-sheet structure characteristic of amyloids and was therefore considered to have the property of oxygenating only amyloids without reacting with functional proteins. Compound (1a) (100 mmol %) was added to amylin, and the mixture was irradiated with light (wavelength: 500 nm) under physiological conditions (pH 7.4, 37° C.). As a result, time-dependent oxygenation at His-18 residue was observed (FIGS. 6a and 7a to 7c). Accordingly, amyloid selectivity was then studied (FIG. 6b). Only a trace amount of an oxygenated form was detected in a sample consisting principally of amylin in a monomeric state (pre-incubation=0 h). On the other hand, when amylin aggregated in advance by pre-incubation before oxygenation reaction was used, the ratio of oxygenized amylin was elevated after reaction with compound (1a) as the pre-incubation time was prolonged to 1 hour and 2 hours. These results suggested that the compound (1a) selectively reacts with aggregated amylin without acting on monomeric amylin. By contrast, riboflavin used had no selectivity and rather had high oxidative activity against monomeric amylin. In fluorescence assay using Nile Red, His$^{18}$-oxygenized amylin had remarkably lower aggregability than that of native amylin (FIG. 6c). Transition to a β-sheet structure was also suppressed as compared with native amylin (FIG. 6d). These results demonstrated that the compound (1a) can catalyze the selective oxygenation of a pathogenic amyloid protein without acting on proteins having physiological roles (FIG. 6e) and indicated that the compound of the present invention can be widely applied to general amyloids.

Example 4

(Selectivity of Oxygenation Reaction Catalyzed by Compound of the Present Invention)

To a phosphate buffer solution (10 mM, pH 7.4) containing Aβ1-42 (20 μM), angiotensin IV (20 μM), methionine enkephalin (20 μM), desacyl ghrelin (20 μM), or somatostatin (20 μM) pre-incubated at 37° C. for 6 hours, riboflavin (4 μM), compound (a) (20 μM), or compound (1a) (4 μM) was added, and the mixture was incubated at 37° C. for 60 minutes under irradiation with LED (wavelength: 500 nm). Then, the reaction was monitored with a mass spectrometer (MALDI-TOF MS) or LC/MS (ESI-Q).

The results of studying the Aβ selectivity of oxygenation reaction are shown in FIG. 8. Riboflavin (20 mmol %), compound (a) (100 mmol %), and compound (1a) (20 mmol %) caused the oxygenation of Aβ at the same level (50 to 70%) under light irradiation conditions of 1 hour in a neutral buffer solution (37° C.). On the other hand, under the same conditions as above, riboflavin and compound (a) caused approximately 20 to 35%, 40 to 70%, 15 to 30%, and 60 to 80% oxygenation of angiotensin IV (VYIHPF (SEQ ID NO: 2)), methionine enkephalin (YGGFM (SEQ ID NO: 3)), desacyl ghrelin (GSSFLSPEHQRVQQRKESKKPPAK-LQPR (SEQ ID NO: 4)), and somatostatin (AGCKNFFWK-TFTSC (SEQ ID NO: 5)), respectively, whereas the generation of an oxygenated form in each reaction using compound (1a) was reduced to 2° or less. These results suggested that riboflavin and compound (a) catalyzes the oxygenation of various substrates by light irradiation, regardless of amyloid or non-amyloid proteins, whereas the compound (1a) rarely has oxidative activity against ordinary substrates, but selectively catalyzes the oxygenation of aggregated Aβ.

Example 5

(Compound of the Present Invention Selectively Binds to Cross-β-Sheet Structure for Oxygenation)

(1) Thioflavin T was added to each of 4 types of aggregated Aβ1-42 prepared by the incubation of Aβ1-42 (20 μm) in a phosphate buffer solution (10 mM, pH 7.4) at 37° C. for 0, 1, 3, and 6 hours, respectively, followed by the measurement of fluorescence intensity. Also, their shapes were analyzed using an atomic force microscope.

As a result, as shown in FIG. 9a, no fluorescence was exhibited in the non-incubated sample (0 h). On the other hand, fluorescence was exhibited in all of the samples incubated for 1, 3, and 6 hours, and stronger fluorescence was observed for the longer incubation times. No aggregation was observed in the non-incubated sample (0 h), whereas oligomer (1 h), protofibril (3 h), and robust fibril (6 h) were observed in the samples incubated for 1, 3, and 6 hours, respectively.

(2) Compound (1a) (10 µM) was added to each of solutions containing 4 types of aggregated Aβ1-42 (0.5 µM) prepared by the incubation of Aβ1-42 (20 µM) in a phosphate buffer solution (10 mM, pH 7.4) at 37° C. for 0, 1, 3, and 6 hours, respectively, followed by the measurement of the fluorescence intensity of compound (1a).

As a result, as shown in FIG. 9b, no fluorescence was exhibited in the non-incubated sample (0 h). On the other hand, fluorescence was exhibited in all of the samples incubated for 1, 3, and 6 hours, and stronger fluorescence was observed for the longer incubation times. The compound (1a) was found to bind to the cross-β-sheet structure of aggregated Aβ1-42.

(3) Riboflavin (4 µM) or compound (1a) (10 µm) was added to each of solutions containing 4 types of aggregated Aβ1-42 (0.5 µM) prepared by the incubation of Aβ1-42 (20 µM) in a phosphate buffer solution (10 mM, pH 7.4) at 37° C. for 0, 1, 3, and 6 hours, respectively, and the mixture was incubated at room temperature for 10 minutes under irradiation with LED (wavelength: 500 nm). Then, the reaction was monitored with a mass spectrometer (MALDI-TOF MS). Also, thioflavin T was added to each prepared aggregated Aβ1-42, followed by the measurement of its fluorescence intensity.

Increase of the intensity ratio of oxygenation (%) was calculated according to (Intensity ratio of oxygenation of aggregated Aβ1-42 (incubated at 37° C. for the predetermined time))−(Intensity ratio of oxygenation of aggregated Aβ1-42 (incubated at 37° C. for 0 hours)).

The intensity ratio of oxygenation (%) was calculated according to (Total intensity of oxygen adducts)/((Intensity of non-oxygen adduct (native))+(Total intensity of oxygen adducts)).

As a result, as shown in FIG. 9c, when compound (1a) was used, increase of the intensity ratio of oxygenation was observed with increase in the fluorescence intensity of thioflavin T (corresponding to a cross-β structure content). When riboflavin was used, no increase of the intensity ratio of oxygenation was observed.

The results (1) to (3) described above demonstrated that the oxygenation efficiency of the compound (1a) is increased with increase in cross-β structure content and supported the idea that such properties are absent in riboflavin and are functions unique to the compound (1a).

Example 6

(Selective Oxygenation of Aβ Oligomer and Aβ Aggregate)

(1) Two types of Aβ1-42 prepared by the incubation of Aβ1-42 (20 µM) in a phosphate buffer solution (10 mM, pH 7.4) at 0° C. (sample E) and room temperature (sample F), respectively, for 24 hours, were each analyzed for size distribution using an atomic force microscope.

As a result, as shown in FIG. 10a, homogeneous oligomers were observed in both of the Aβ1-42 samples prepared incubated at 0° C. and room temperature. The Aβ1-42 oligomer prepared by incubation at room temperature was observed as an oligomer having a larger size.

(2) Compound (1a) (10 µM) was added to each of solutions containing two types of Aβ1-42 oligomers (0.5 µM) prepared by the incubation of Aβ1-42 (20 µM) in a phosphate buffer solution (10 mM, pH 7.4) at 0° C. and room temperature, respectively, for 24 hours, followed by the measurement of the fluorescence intensity of compound (1a).

As a result, as shown in FIG. 10b, fluorescence was exhibited in both of the Aβ1-42 oligomers prepared by incubation at 0° C. and room temperature, demonstrating that the compound (1a) binds to the Aβ1-42 oligomer. The Aβ1-42 oligomer prepared by incubation at room temperature exhibited stronger fluorescence.

(3) Compound (1a) (4 µM) was added to each of solutions containing two types of Aβ1-42 oligomers (0.5 µM) prepared by the incubation of Aβ1-42 (20 µM) in a phosphate buffer solution (10 mM, pH 7.4) at 0° C. and room temperature, respectively, for 24 hours, and the mixture was incubated at room temperature for 10 minutes under irradiation with LED (wavelength: 500 nm). Then, the reaction was monitored with a mass spectrometer (MALDI-TOF MS).

The intensity ratio of oxygenation (%) was calculated according to (Total intensity of oxygen adducts)/((Intensity of non-oxygen adduct (native))+(Total intensity of oxygen adducts)).

As a result, as shown in FIG. 10c, the compound (1a) was found to be able to catalyze the oxygenation of both of the Aβ1-42 oligomers prepared by incubation at 0° C. and room temperature. The Aβ1-42 oligomer prepared by incubation at room temperature exhibited larger oxygenation intensity.

(4) Compound (1a) (4 µM) was added to each of solutions containing two types of Aβ1-42 oligomers (0.5 µM) prepared by the incubation of Aβ1-42 (20 µM) in a phosphate buffer solution (10 mM, pH 7.4) at 0° C. and room temperature, respectively, for 24 hours, and the mixture was incubated at room temperature for 1 hour under irradiation with LED (wavelength: 500 nm). Then, each solution was incubated at 37° C., and Nile Red was added thereto, followed by the measurement of its fluorescence intensity. The sample incubated for 6 hours was also analyzed for its shape by atomic force microscopy. A non-oxygenized Aβ1-42 oligomer (native) was prepared without light irradiation.

As a result, as shown in FIG. 10d, compound (1a) exhibited weak fluorescence intensity for both of the Aβ1-42 oligomers prepared by incubation at 0° C. and room temperature as compared with native and was thus found to suppress increase in the cross-β structure of the Aβ1-42 oligomer. Fibril formation was also similarly suppressed.

The results (1) to (4) described above demonstrated that the compound (1a) suppresses aggregation and fibril formation by the oxygenation of the Aβ1-42 fibril structure as well as oligomer structure.

Example 7

(Oxygenating Effect of Compound of the Present Invention on Aggregation of Amyloid Other than Aβ Amyloid)

(1) Compound (1a) (20 µM) was added to a neutral buffer solution containing non-aggregated (incubated for 0 hours) or aggregated (incubated for 12 hours) insulin (160 µm) prepared by the incubation of insulin (400 µM) in a 25 mM hydrochloric acid solution at 60° C. with stirring (1,000 rpm), and the mixture was incubated at 37° C. for 30 minutes under irradiation with LED (wavelength: 500 nm). Then, the reaction was monitored with a mass spectrometer (MALDI-TOF MS).

As a result, as shown in FIG. 11a, the progression of oxygenation was not observed in the non-aggregated insulin and was observed in the aggregated insulin. The oxygenation of the aggregated insulin was not observed without light irradiation.

(2) Compound (1a) (20 μM) was added to a neutral buffer solution containing non-aggregated (incubated for 0 hours) or aggregated (incubated for 24 hours) β2-microglobulin (88 μM) prepared by the incubation of β2-microglobulin (114 μM) in a 1 M hydrochloric acid solution at 37° C. with stirring (1,000 rpm), and the mixture was incubated at 37° C. for 30 minutes under irradiation with LED (wavelength: 500 nm), followed by digestion with endoproteinase (Lys-C). The reaction was monitored with a mass spectrometer (MALDI-TOF MS).

As a result, as shown in FIG. 11b, the progression of oxygenation was not observed in the non-aggregated β2-microglobulin, whereas oxygenation was observed in the aggregated β2-microglobulin. The oxygenation of the aggregated β2-microglobulin was not observed without light irradiation.

(3) Compound (1a) (20 μM) was added to a neutral buffer solution containing non-aggregated (incubated for 0 hours) or aggregated (incubated for 3 hours) transthyretin (36 μM) prepared by the incubation of transthyretin (80 μM, containing 100 mM NaCl) in a 10 mM hydrochloric acid solution at room temperature, and the mixture was incubated at 37° C. for 30 minutes under irradiation with LED (wavelength: 500 nm), followed by digestion with endoproteinase (Lys-C). The reaction was monitored with a mass spectrometer (MALDI-TOF MS).

As a result, as shown in FIGS. 11c to 11e, the progression of oxygenation was not observed in the non-aggregated transthyretin, whereas oxygenation was observed in the aggregated transthyretin. The oxygenation of the aggregated transthyretin was not observed without light irradiation.

(4) Compound (1a) (20 μM) was added to a buffer solution containing non-aggregated (incubated for 0 hours) or aggregated (incubated for 24 hours) α-synuclein (69 μm) prepared by the incubation of α-synuclein (69 μM) in a 20 mM tris buffer solution (pH 7.5, containing 100 mM NaCl and 1 mM $MgCl_2$) at 37° C. with stirring (1,000 rpm), and the mixture was incubated at 37° C. for 30 minutes under irradiation with LED (wavelength: 500 nm), followed by digestion with endoproteinase (Lys-C). The reaction was monitored with a mass spectrometer (MALDI-TOF MS).

As a result, as shown in FIGS. 11f and 11g, the progression of oxygenation was not observed in the non-aggregated α-synuclein, whereas oxygenation was observed in the aggregated α-synuclein. The oxygenation of the aggregated α-synuclein was not observed without light irradiation.

Example 8

(Compound of the Present Invention is Specific for Amyloid Aggregation Associated with Formation of Cross-β-Sheet Structure)

(1) A phosphate buffer solution (10 mM, pH 7.4) containing nucleoside phosphorylase (0.1 mg/mL) was incubated at 60° C. The degree of thermal aggregation was monitored using a fluorescence assay kit (Protein Stability and Aggregation Assay Kit (ProFoldin, Hudson, Mo., USA)).

As a result, as shown in FIG. 12a, as a result of incubating the phosphate buffer solution containing nucleoside phosphorylase, increase in the fluorescence intensity (degree of thermal aggregation) of the kit was observed as the time passed. Samples prepared by incubation for 0 hour and 1 hour were used as non-aggregated and aggregated phosphorylases, respectively, in the oxygenation reaction analysis.

(2) Riboflavin (4 μM) or compound (1a) (4 μM) was added to each of non-aggregated (incubated for 0 hour) and aggregated (incubated for 6 hours) Aβ1-42 prepared by the incubation at 37° C. of a phosphate buffer solution (10 mM, pH 7.4) containing Aβ1-42 (20 μM) preincubated at 37° C., and the mixture was incubated at room temperature for 10 minutes under irradiation with LED (wavelength: 500 nm). Then, the reaction was monitored with a mass spectrometer (MALDI-TOF MS).

Riboflavin (4 μM) or compound (1a) (4 μM) was added to each of non-aggregated (incubated for 0 hour) and aggregated (incubated for 1 hour) nucleoside phosphorylases prepared by the incubation at 60° C. of a phosphate buffer solution (10 mM, pH 7.4) containing nucleoside phosphorylase (0.1 mg/mL), and the mixture was incubated at room temperature for 10 minutes under irradiation with LED (wavelength: 500 nm), followed by digestion with endoproteinase (Lys-C). The reaction was monitored with a mass spectrometer (MALDI-TOF MS).

Each oxygenation ratio was calculated according to (Intensity ratio of oxygenation of aggregated Aβ1-42)/(Intensity ratio of oxygenation of non-aggregated Aβ1-42) and (Intensity ratio of oxygenation of aggregated nucleoside phosphorylase)/(Intensity ratio of oxygenation of non-aggregated nucleoside phosphorylase).

As a result, as shown in FIG. 12b, as a result of adding riboflavin (20.0 mmol %) or compound (1a) (20.0 mmol %) to non-aggregated or aggregated Aβ1-42 and irradiating the mixture with light under physiological conditions (pH 7.4, room temperature), the oxygenation ratio obtained using riboflavin was approximately 0.8, and the oxygenation ratio obtained using compound (1a) was approximately 4.2.

As a result of adding riboflavin or compound (1a) to non-aggregated or aggregated nucleoside phosphorylase and irradiating the mixture with light under physiological conditions (pH 7.4, room temperature), the oxygenation ratio obtained using riboflavin was approximately 1.4, and the oxygenation ratio obtained using compound (1a) was approximately 1.2.

The results (1) and (2) described above demonstrated that the compound (1a) specifically acts on amyloid aggregation associated with cross-β structure formation (not on thermal aggregation).

Example 9

Compound (1a) (20 μM) or riboflavin (4 μM) was added to a culture medium containing L-ascorbic acid (500 μM), and the mixture was incubated at 37° C. for 30 minutes under irradiation with LED (wavelength: 500 nm). Then, the reaction was monitored with a mass spectrometer (LC-MSMS).

As a result, as shown in FIG. 13, as a result of adding compound (1a) (4.0 mmol %) or riboflavin (0.8 mmol %) to L-ascorbic acid and irradiating the mixture with light, 100° of the L-ascorbic acid remained when the compound (1a) was used. On the other hand, the L-ascorbic acid disappeared completely when riboflavin was used.

These results demonstrated that the compound of the present invention does not exhibit its oxidative effect by mere light irradiation and exhibits the oxidative effects only by binding to the cross-β-sheet structure as in amyloid aggregation.

The invention claimed is:

1. A benzothiazole compound represented by formula (1):

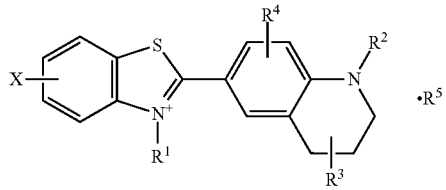

(1)

wherein
X represents a halogen atom;
R¹ represents an optionally substituted hydrocarbon group;
R² represents a hydrogen atom or an optionally substituted hydrocarbon group;
R³ and R⁴ each independently represent a hydrogen atom, an optionally substituted hydrocarbon group, an alkoxy group, a halogen atom, an amino group, a nitro group, or a cyano group;
R² and R⁴ optionally together form an alkylene group; and
R⁵ represents an anion.

2. The benzothiazole compound according to claim 1, wherein at least one selected from the group consisting of R¹, R², R³, and R⁴ is a substituted hydrocarbon group having 1 to 3 substituents each independently selected from the group consisting of a halogen atom, an amino group, a nitro group, a cyano group, an alkoxy group, an acyl group, a carboxyl group, an alkoxycarbonyl group, an aromatic hydrocarbon group, and a heterocyclic group.

3. The benzothiazole compound according to claim 1, wherein R¹ is an alkyl or alkenyl group having 1 to 12 carbon atoms.

4. The benzothiazole compound according to claim 1, wherein R¹ is an alkyl group having 1 to 12 carbon atoms.

5. The benzothiazole compound according to claim 1, wherein R³ is a hydrogen atom or an alkyl or alkenyl group having 1 to 12 carbon atoms.

6. The benzothiazole compound according to claim 1, wherein R³ is a hydrogen atom.

7. The benzothiazole compound according to claim 1, wherein R² forms a $C_2$-$C_4$ alkylene group together with R⁴, or is an alkyl or alkenyl group having 1 to 12 carbon atoms, the alkyl or alkenyl group optionally having a carboxyl group, an alkoxycarbonyl group, a carbamoyl group, or a dipeptide- to hexapeptide-CO— group, and the carbamoyl group or dipeptide to hexapeptide optionally having 1 or 2 groups selected from the group consisting of a $C_{6-14}$ aryl group and an alkoxycarbonyl group.

8. A pharmaceutical composition comprising the benzothiazole compound according to claim 1 and a pharmaceutically acceptable carrier.

9. A method for oxidizing Aβ peptide in a subject in need thereof, comprising administering the compound according to claim 1 to the subject in need thereof.

10. A method according to claim 9, wherein the subject has a disease selected from the group consisting of as Alzheimer's disease, Parkinson's disease, diabetes mellitus, Huntington's disease, and systemic amyloidosis.

11. The benzothialzole compound according to claim 1, which is compound (1a):

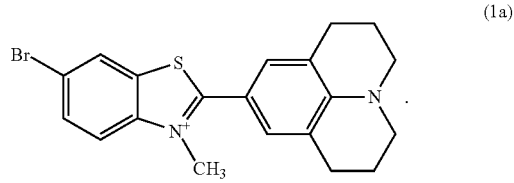 [SMILES: C[n+]1c(-c2cc3c4c(c2)CCCN4CCC3)sc2cc(Br)ccc21]

(1a)

12. The benzothiazole compound according to claim 1, which is compound (1b), compound (1c), compound (1d), or compound (1e):

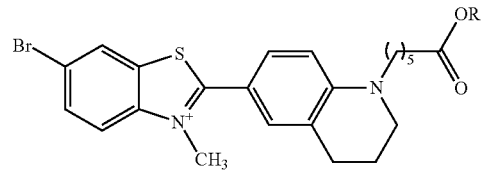

R = CH₃(1b)
R = H(1c)

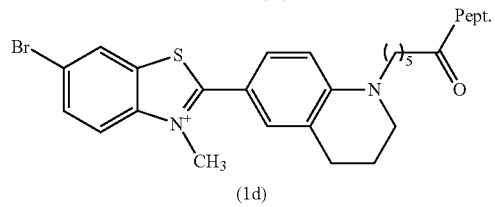

(1d)

Pept.:D-[K(Boc)LVF(4-Ph)F](1d)
Pept.:D[KLVF(4Ph)F](1e)

* * * * *

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Artificial peptide

<400> SEQUENCE: 1

Lys Leu Val Phe Phe
1               5

<210> SEQ ID NO 2
<211> LENGTH: 6
<212> TYPE: PRT
<213> ORGANISM: Artificial sequence
<220> FEATURE:
<223> OTHER INFORMATION: Artificial peptide

<400> SEQUENCE: 2

Val Tyr Ile His Pro Phe
1               5

<210> SEQ ID NO 3
<211> LENGTH: 5
<212> TYPE: PRT
<213> ORGANISM: Artificial sequence
<220> FEATURE:
<223> OTHER INFORMATION: Artificial peptide

<400> SEQUENCE: 3

Tyr Gly Gly Phe Met
1               5

<210> SEQ ID NO 4
<211> LENGTH: 28
<212> TYPE: PRT
<213> ORGANISM: Artificial Sequence
<220> FEATURE:
<223> OTHER INFORMATION: Artificial peptide

<400> SEQUENCE: 4

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 5
<211> LENGTH: 14
<212> TYPE: PRT
<213> ORGANISM: Artificial Sequence
<220> FEATURE:
<223> OTHER INFORMATION: Artificial peptide

<400> SEQUENCE: 5

Ala Gly Cys Lys Asn Phe Phe Trp Lys Thr Phe Thr Ser Cys
1               5                   10
```